United States Patent [19]
Stoker et al.

[11] Patent Number: 5,807,321
[45] Date of Patent: Sep. 15, 1998

[54] SYSTEM FOR ELECTRONICALLY MONITORING THE DELIVERY OF CONTRAST MEDIA

[75] Inventors: Ronald L. Stoker, South Jordan; Darryl Kent Backman, Salt Lake City; Christopher L. Durham, Salt Lake City; Jerrold L. Foote, Salt Lake City; Garlyn W. Hendry, Salt Lake City; Gregory R. McArthur, Sandy; Jon Rhees, Riverton; Thomas D. Stout; Steve R. Taylor, both of Salt Lake City; William Woelper, Sandy, all of Utah

[73] Assignee: Merit Medical, South Jordan, Utah

[21] Appl. No.: 563,361

[22] Filed: Nov. 28, 1995

[51] Int. Cl.⁶ .................................................. A61M 31/00
[52] U.S. Cl. ............................................. 604/65; 604/251
[58] Field of Search .................... 128/DIG. 12, DIG. 13; 604/65–67, 80–81, 30–34

[56] References Cited

U.S. PATENT DOCUMENTS

| | | |
|---|---|---|
| 4,553,964 | 11/1985 | Sasaki . |
| 4,673,397 | 6/1987 | Lynn et al. . |
| 4,710,166 | 12/1987 | Thompson et al. ........................ 604/65 |
| 4,734,091 | 3/1988 | Boyle et al. . |
| 4,845,487 | 7/1989 | Frantz et al. ............................... 604/67 |
| 4,854,323 | 8/1989 | Hirschman et al. ....................... 604/67 |
| 4,946,439 | 8/1990 | Eggers ............................ 128/DIG. 13 |
| 5,087,245 | 2/1992 | Doan ......................................... 604/67 |
| 5,100,380 | 3/1992 | Epstein et al. ............................. 604/67 |
| 5,328,463 | 7/1994 | Barton et al. . |
| 5,356,375 | 10/1994 | Higley . |
| 5,382,232 | 1/1995 | Hague et al. .............................. 604/65 |
| 5,423,346 | 6/1995 | Daoud . |
| 5,423,751 | 6/1995 | Harrison et al. . |

*Primary Examiner*—Manuel Mendez
*Attorney, Agent, or Firm*—Workman, Nydegger & Seeley

[57] ABSTRACT

A system and method for electronically monitoring and displaying digital flow data relevant to the administration of a parenteral fluid, such as a contrast medium, to a patient is disclosed. The system includes a disposable fluid flow indicator, adapted to be detachably connected in fluid communication with a contrast media source. The fluid flow indicator measures the amount of contrast media dispensed from the source and administered to a patient, and provides an indication of the amount dispensed based on the movement of a displacement indicator.

Also disclosed is an electronic controller, which is adapted to be detachably connected to the fluid flow indicator. The controller includes a sensor interface circuit, which operably interfaces the electronic controller circuitry with the fluid flow indicator so that the fluid flow measurement indicator is optically detected by the sensor circuit, which in turn generates a representative electrical flow signal. The electrical flow signal is received and processed by a programmable digital processor contained within the electronic controller in a manner so as to continuously track and generate digital flow data. The digital flow data includes information regarding the amount of contrast medium remaining within the contrast source, and the amount of medium that has been delivered to the patient. The electronic controller also includes a digital display, which continuously displays the digital flow data. The controller also includes a series of user actuable switches, which permit the user to select various functions to be performed by the digital processor, including the ability to display digital flow data for prior patients, and the ability to select various operating parameters. Since the electronic controller is detachably connected to the flow indicator, the controller can be reused at the completion of a monitoring procedure.

Also disclosed is a method for safely and efficiently monitoring and displaying the amount of contrast medium administered to a patient by using a programmable digital processor.

41 Claims, 11 Drawing Sheets

SYSTEM FOR ELECTRONICALLY MONITORING THE DELIVERY OF CONTRAST MEDIA

BACKGROUND OF THE INVENTION

1. The Field of the Invention

This invention relates to a system for monitoring the delivery of parenteral fluids, and more particularly, to a system for electronically monitoring, tracking and displaying data that pertains to the administration of a contrast medium to a patient.

2. The Relevant Technology

In many medical procedures, medical personnel have a need to view a patient's internal organs or tissues using radiological techniques. However, due to their lucent characteristics, a clear view of human tissue and organs is not often obtainable with standard X-rays. Thus, a clinician will first inject a radiopaque substance into the area of interest. This radiopaque material, typically referred to as a "contrast medium," provides a contrast in density between the tissue or organ being filmed and the medium, thereby providing a clearer, and more useful view to the clinician. For instance, one form of contrast medium, barium sulfate, will when swallowed help to demonstrate the outline of the intestinal tract as X-ray films are taken during the passage of the medium. Other organs, tissue areas, blood vessels, etc. can similarly be viewed, thereby providing the doctor with an improved, and more accurate view of the patient's condition.

Although contrast media can be delivered in a variety of ways depending on the portion of the body to be viewed, one widely used delivery technique is the catheter. A catheter can be used to deliver the contrast medium to canals, vessels, passageways or other body cavities that can not otherwise be reached by oral ingestion. In some procedures, the contrast medium may also be used in association with dilatation catheters, in which case the contrast medium is contained within the catheter rather than being delivered into the patient.

Regardless of the means of delivery, a concern common to all procedures utilizing any type of contrast medium is the extremely high cost of the medium itself. Thus, it is very important to dispense the medium precisely and in a manner that results in the least amount of waste. Further, for accurate billing and cost assessment purposes, it is of great importance for the clinician to be able to monitor and keep track of the exact amount of medium that has been dispensed to a particular patient over the course of a procedure or hospital stay.

In addition to cost concerns, there are also safety concerns associated with the administration of a contrast medium via a catheter. As with any intravenous administration of a fluid, it is critical that air bubbles not be inadvertently injected into the patient's vascular system. If bubbles are introduced into a patient, major complications, and even death, can result. Thus, as the contrast medium is introduced into the catheter, it is extremely important that the clinician be cognizant of the amount of medium remaining in the container. When the container is empty, or near empty, the clinician must be careful so as to not continue the injection process to the point where air is introduced into the catheter.

Contrast medium is typically distributed in bottles or drip-bags, as is shown in the typical prior art system illustrated in FIG. 1 of the appended drawings. FIG. 1 illustrates a contrast media bag 10, which typically is hung from an IV pole 12 and is contained integrally within a cuff assembly 14. The cuff assembly acts as a pressurizer when hand pump 16 is used to inflate the cuff 14. Pump valve 18 allows for inflation and deflation of cuff 14.

Connected to the contrast media bag 10, is a bag connection assembly 20 and an inlet line 22. When hand pump 16 is squeezed, cuff 14 is inflated and applies pressure to contrast media bag 10. This causes the contrast medium to flow into out of the bag 10 and exit into the inlet line 22. A series of valves (shown here at 24, 26, 28) are typically disposed within the inlet line 22 so as to control the flow of the contrast media, and to prevent contrast media from re-entering and contaminating the contrast media contained in contrast media bag 10. Also connected to the inlet line is a reservoir 30, into which the contrast media flows from contrast media bag 10 when the valve 24 is opened.

In general operation, contrast medium flows out of the reservoir 30 through an outlet line 32 to a fluids administration system designated generally at 34, which typically includes a standard syringe 36 connected to a catheter manifold 38. Connected to the catheter manifold 38 is a catheter connection assembly 40, to which is connected a catheter (not shown). Various fluids, including a contrast medium, would pass through catheter manifold 38 to the catheter and then intracorporeally to a patient. When administering contrast media to the patient, the manifold 38 is appropriately configured (by opening and closing the appropriate manifold valves (42,44,46), and contrast medium is then drawn from the media bag 10, via the reservoir 30, and into the barrel 48 of syringe 36 by retracting the syringe plunger 50. When syringe 36 is filled to the desired level, the contrast medium is then injected into the patient. The act of filling syringe 36 to the desired level and injecting the contrast medium into the patient is commonly referred to as administering a "bolus" of contrast media. In a typical procedure, a number of boluses are administered to a patient.

Delivery of contrast medium from this, or similar, types of systems can result in a variety problems—both in terms of patient safety and delivery efficiency. First, while delivering the contrast medium to a patient during a procedure, the medical technician must monitor the amount of medium that remains in the contrast media source (shown in FIG. 1 as a contrast media bag 10) so as to avoid emptying it and inadvertently injecting air bubbles into the patient. This, of course, can only be done by visually monitoring and continually assessing the amount of medium that remains in the bag 10 throughout the procedure. Such visual monitoring is inaccurate and prone to error, and exposes the patient to some risk. Further, the need to constantly observe the contents of the contrast media bag 10 diverts attention away from the patient, and is thus distracting and adds unnecessary complexity to the overall procedure.

In addition to raising safety concerns, the use of a standard contrast media bag or bottle can be extremely inefficient. The cumulative amount of contrast medium administered from a standard contrast media bag or bottle to a specific patient—the number of boluses—is difficult to monitor, especially when multiple bottles are used, or if one bottle is used between two different patients. This inability to accurately keep track of exactly how much medium has been administered to a particular patient can result in the patient being incorrectly charged. Under billing, of course, can result in financial losses to the medical facility performing such procedures. Further, the difficulty in determining the useful amount of medium in a particular bottle often results in the remainder being discarded, rather than being used on a new patient. Given the very high cost of contrast medium, such waste can also translate into significant financial losses—especially in a facility that performs a large number of these types of procedures. Given today's concern with high medical costs, these inefficiencies are of course undesirable, and procedures and apparatus for minimizing the amount of contrast media that is wasted are needed.

SUMMARY AND OBJECTS OF THE INVENTION

The system and method of the present invention have been developed in response to the present state of the art, and in particular, in response to the problems and needs that have been associated with the delivery of a contrast medium to a patient via a catheter. However, it is not intended that the system and method of the present invention will necessarily be limited solely to the delivery of contrast media, since they will also find useful application with potentially many kinds of procedures which require the accurate, safe and precise delivery of parenteral fluids. In order to solve the problems known in the art, as stated above, it is a primary object of the present invention to provide a system for automatically and electronically monitoring the amount of parenteral fluid, such as a contrast medium, that is delivered from a parenteral fluid source to a specific patient.

Another important object of the present invention is to provide a system and method whereby state of the art electronic technology can be utilized to assist the medical technician in accurately measuring, monitoring and recording the amount of contrast medium that has been dispensed to a particular patient and/or that has been dispensed from a particular contrast media source, and which will at the same time automatically electronically record and store data pertaining to a particular patient and/or contrast media source for later reference.

Yet another important object of the present invention is to provide a system and method that electronically displays in real time the amount of contrast medium that remains unused in a contrast media source.

A related object of the present invention is to provide a system and method that electronically displays in real time the amount of contrast medium that has been dispensed to a patient.

A further object of the present invention is to provide a system and method that allows a user to selectively display and review the amount of contrast medium that has been dispensed to previous patients.

It is another object of the present invention to provide a system and method that is capable of electronically monitoring the amount of contrast medium that has been dispensed from a contrast media source and that can alert the technician when the media source is nearly empty.

Another object of the present invention is to provide an electronic monitoring and recording system for contrast media that utilizes an electronic controller that can be operatively attached and detached to a disposable fluid flow indicator, so that the electronic controller can be reused.

These and other objects, features and advantages of the present invention will become more fully apparent from the following, more detailed description which follows, taken in conjunction with the drawings and claims, or from practice of the invention itself.

Briefly summarized, the foregoing and other objects are achieved in a parenteral fluid monitoring system and method that includes a microprocessor-based electronic controller monitoring device paired with a disposable fluid flow indicator means. The primary purpose of the monitoring system and associated method is to monitor contrast medium flow from a bag or bottle and to display associated information for the clinician's convenience.

The fluid flow indicator means is attached in fluid communication with the tubing used to transport the contrast medium from the bottle or bag to a delivery mechanism, such as a catheter disposed within a patient. The fluid flow indicator means measures and provides an indication of the amount of fluid that is dispensed to the patient's catheter, which is usually accomplished by way of a syringe.

In the preferred system, the microprocessor-based electronic controller is capable of being detachably and operatively connected to the flow indicator means, which is disposed of after each patient procedure. In this way, the electronic controller can be repeatedly reused, thereby reducing the overall cost of each procedure. Preferably, the electronic controller includes a sensor means. When the fluid flow indicator is operatively attached to the electronic controller, the sensor means detects the amount of fluid dispensed through the tubing as measured and indicated by the flow indicator, and then generates an electrical flow signal that is representative of that amount.

Disposed within the electronic controller is a programmable digital processor means that is programmed to receive and automatically process the electrical flow signal so as to derive therefrom digital flow data. In the preferred embodiment, the digital flow data includes remnant data, which is representative of the magnitude of the total amount of parenteral fluid remaining within the parenteral fluid source; and dosage amount data, which is representative of the magnitude of the total amount of parenteral fluid that has been delivered to the patient.

In addition to continuously tracking digital flow data for a current patient, the digital processor is also programmed to store digital flow data in a data memory means and thereby maintain historical data values for prior patients.

Digital flow information is continuously provided to the medical clinician by way of an electronic display means, which is incorporated within the electronic controller. In this way, the medical technician can continuously and precisely monitor the amount of contrast medium that has been administered to the current patient, and that remains within the media source. This enables the technician to insure that the correct amount of contrast has been dispensed, and also permits for extremely accurate record keeping, inventory control and billing.

In addition to visually displaying the amount of fluid that remains within the current contrast media fluid source, the electronic controller preferably includes an audible alarm means, which is activated when the amount of fluid remaining falls below a predetermined amount. In this way, the medical technician does not need to continuously glance at the fluid source or the electronic controller display to keep track of the remaining amount of contrast medium. Instead, the alarm will sound, indicating that the current bottle should be replaced before any additional dispensing occurs. This provides an extra level of safety, insuring that the patient is not inadvertently injected with air bubbles from an empty media bottle or bag.

The detachable and reusable electronic controller also includes a switch means, which the system user can selectively operate so as to choose any one of a variety of functions to be performed by the digital processor means. Optional functions generally include the ability to select which of the digital flow data is displayed, and the ability to retrieve and display historical digital flow data stored for previous patients. The switch means further allows the user to enter and save certain variables in the electronic controller, such as the size of a new parenteral fluid source.

BRIEF DESCRIPTION OF THE DRAWINGS

The presently preferred embodiments and the presently understood best mode of the invention will be described with additional detail through the use of the accompanying drawings, wherein corresponding parts are designated by the same reference numerals throughout, and in which.

DETAILED DESCRIPTION OF THE PREFERRED EMBODIMENTS

The following detailed description is divided into two parts. In Part I, a preferred embodiment of the overall system of the present invention is described, including a detailed description of the electronic controller and the flow indicator, by reference to FIGS. 2–7. In Part II, the presently preferred method by which the system is used to electronically monitor, track, display and record flow data pertaining to the administration of a parenteral fluid, such as a contrast medium, is described, including a detailed description of one presently preferred method for programming the microcontroller and the digital processor used in the electronic controller. This is done by making specific reference to FIGS. 8 and 9A–9C.

I. THE SYSTEM.

A. General Environment and Intended Utility of the System.

A noted above, the system and method of the present invention have been developed in response to specific needs which exist in connection with current techniques used to deliver parenteral fluids to a patient. As already described in connection with FIG. 1, the use of currently available techniques to deliver such parenteral fluids, such as a contrast medium, is often inconvenient, inefficient and potentially unsafe.

While the system and method of the present invention are particularly useful in connection with the administration of a contrast medium to a catheter and then intracorporeally to a patient, the present invention is not intended to be necessarily limited to use in connection with contrast media. Rather, it is contemplated that the system and method of the invention will find useful application with respect to medical procedures requiring the accurate, safe, and convenient administration of a parenteral fluid to a patient.

While a number of different types of systems have been developed for administering a parenteral fluid to a patient, the monitoring system of the present invention can be used in connection with most any environment where a parenteral fluid, as for example a contrast medium, is dispensed from a parenteral fluid source to a patient through a fluid conduit. Thus, the system could be used, for example, in connection with the contrast medium delivery set-up illustrated and generally described above in connection with FIG. 1.

Figure 2:
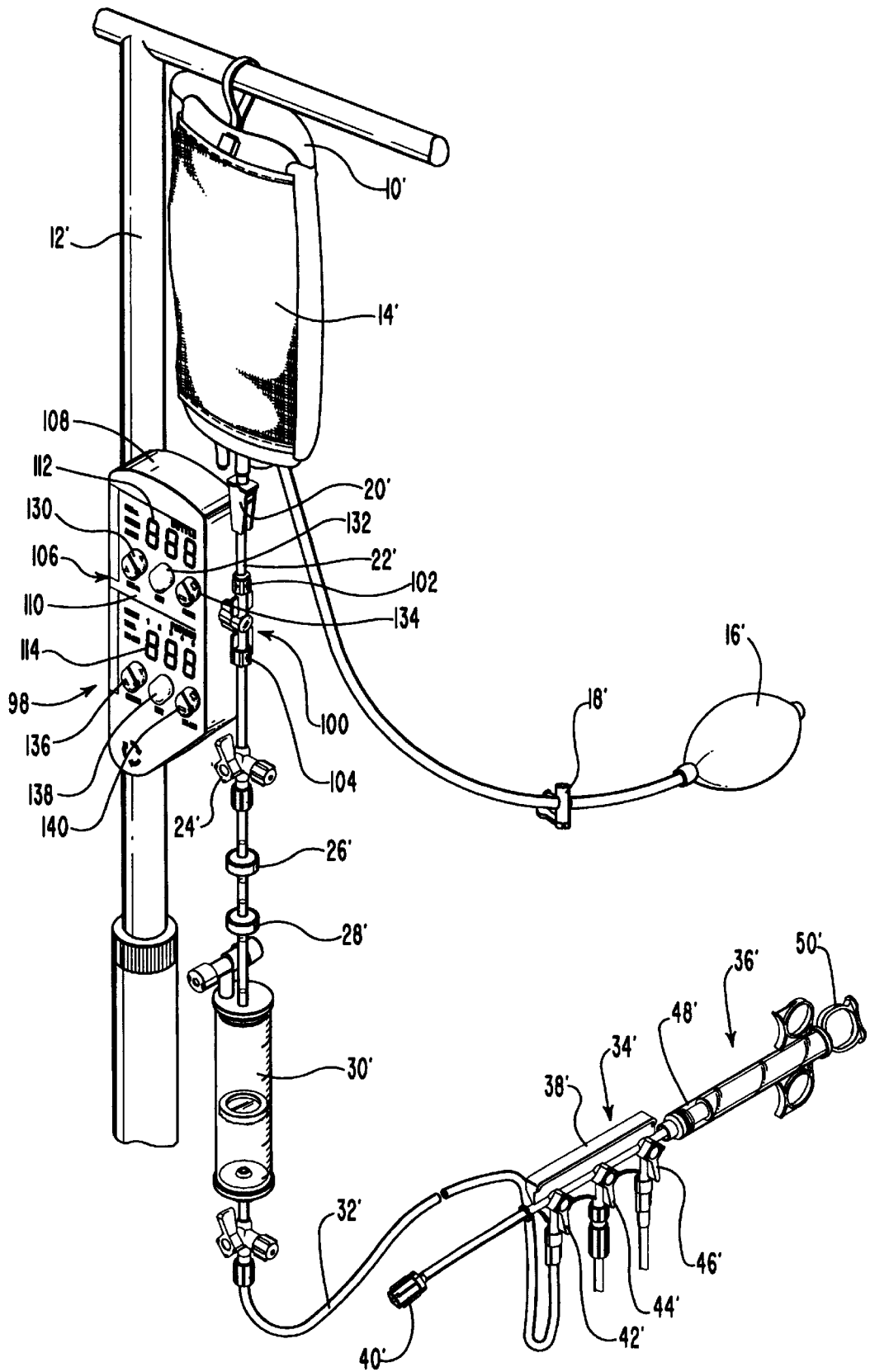
FIG. 2 is a perspective view of the inventive contrast media delivery system as it would be used in a typical application.

FIG. 2 also illustrates a suitable environment, also used for the management and administration of contrast media, in which the monitoring system of the present invention could be used. The environment illustrated in FIG. 2 is of the type disclosed in pending U.S. patent application Ser. No. 08/509,926, filed Aug. 1, 1995, and entitled "Apparatus and Method for Managing Delivery of Contrast Media," which is assigned to the same assignee as the present application and which is incorporated herein by reference. A detailed description of the operation and structure of that system will not be repeated here.

As is shown in FIG. 2, contrast medium is typically stored and dispensed directly from a contrast media bottle, or bag 10', which is hung from a standard IV pole 12'. The bag 10' is typically disposed within an air-inflatable cuff assembly 14', which is operable by way of hand pump 16'. Inflation of the cuff assembly 14' ensures the contrast medium flows out of the bag 10', and into a fluid conduit that ultimately communicates the contrast medium with the patient, usually via an indwelling catheter (not shown). While this fluid conduit could be implemented in a variety of ways, in the system illustrated in FIG. 2, it is formed, for example, by medical tubing, which is typically interconnected by way of a series of valves (24', 26', and 28'), an intermediate chamber 30', a fluids administration system 34', and a catheter connection assembly 40', which is then connected to the indwelling catheter (not shown).

The contrast medium flows out of the bag 12' and into medical tubing, shown at inlet line 22', and continues to flow through appropriately configured valve 24' and one-way valves 26', 28', and then into a reservoir 30'. The opposite output end of the reservoir 30' is in turn connected to the fluids administration system, designated at 34', which operates in the manner previously described. Connected at the output of fluids administration system 34' is a standard catheter connection assembly 40', to which is connected a catheter (not shown).

The actual administration of the contrast medium to the patient proceeds in the same general manner as described above. Typically, the fluid administration assembly 34' includes a means for facilitating the withdrawal of the medium from the bag 12', and for then dispensing it to the patient, such as a standard syringe assembly 36'. The barrel 48' of syringe 36' is connected in fluid communication with the fluid conduit, such that when the plunger 50' is retracted, contrast medium is drawn from the bag 12', and into the syringe barrel 36'. The medium is then administered to the patient by injecting the plunger 50' back into the barrel 48', causing the medium to flow through the catheter connection 40' and into the catheter. This process is repeated until a sufficient amount of medium has been administered.

B. The Presently Preferred Monitoring System, Electronic Controller and Fluid Flow Indicator: FIGS. 2 through 7.

The electronic monitoring system of the present invention is comprised of a fluid flow indicator means, which indicates the amount of contrast medium that is being dispensed to the patient through the fluid conduit. The fluid flow indicator means is thus preferably connected in fluid communication with the fluid conduit connecting the contrast medium source bag 12', to the patient. The system also includes an electronic controller, which in turn is comprised of a digital processor means. The digital processor means is programmed so as to receive the measured amount of contrast medium dispensed through the fluid conduit as indicated by the flow indicator means, and to then process the amount measured so as to electronically monitor, display and record digital flow data. In the preferred embodiment, this digital flow data includes, for example, data that is representative of the amount of contrast medium that remains within the contrast media source 12', referred to herein as the "remnant" data value, and the amount of contrast medium delivered to the patient, referred to herein as the "dosage amount" data value. Also included as part of the electronic controller is a display means, electronically connected to the digital processor means, for outputting a visually perceivable display of the digital flow data generated by the processor means.

FIG. 2 illustrates an example of one presently preferred embodiment of the monitoring system of the present invention designated generally at 98. By way of example, and not limitation, the fluid flow indicator means is shown as preferably comprising a positive displacement device, shown generally at 100. This device 100 provides an indication as to the amount of contrast medium that is being dispensed to the patient, based upon the amount of fluid that is displaced through the device 100.

As is further shown in FIG. 2, positive displacement device 100 is connected downstream from the contrast media bag 12', and is connected in fluid communication with the fluid conduit by being connected directly in-line with the inlet line 22' tubing. Preferably, this is done by way of standard Luer connectors 102 and 104, or any similar connection scheme that allow easy attachment and detachment of the displacement device 100. It will be appreciated that while the displacement device 100 is shown as being connected at a specific point along the fluid conduit (i.e., at inlet line 22'), it could be connected at most any point along the fluid communication path. For example, it could be mounted to the fluid administration system 34', or at practically any other convenient point along the fluid conduit between the media bag 12' and the catheter connector 40'. Additional details pertaining to the preferred structure and operation of the positive displacement device 100 will be provided below.

While in the preferred embodiment the fluid flow indicator means is illustrated and described as a positive displacement device 100, it should be appreciated that the preferred embodiment is illustrative only, and is not to be construed as limiting the scope of the invention. For example, a number of different types of devices could be utilized to implement the function provided by the fluid flow indicator means, including pressure and/or weight transducers, flow meters (as for example that which is described in U.S. Pat. No. 5,337,615), thermistors, magnetic flux detectors, flow turbines, and rate-of-flow detectors—all of which can be used to provide some indication as to the amount of fluid that is flowing through a fluid conduit.

FIG. 2 also illustrates, by way of example, one presently preferred embodiment of the detachable and reusable electronic controller, shown generally at 106. Preferably, the electronic controller 106 includes a means for providing a detachable connection to the IV pole 12', such as a spring loaded clamp (not shown), or any other connection scheme that allows for easy attachment and removal of the controller 106. Disposed integrally within the electronic controller housing 108 is the digital processor means, comprised of a programmable digital microprocessor (shown at 220 in FIG. 7), which is described in further detail below in connection with FIG. 7. As noted above, the programmable digital processor 220 is programmed to electrically process the measured amount of contrast medium indicated by the positive displacement device 100, so as to electronically monitor, display and record the digital flow data. In the preferred embodiment, the digital processor 220 calculates and monitors the amount of contrast medium that has been delivered from, and that remains within, the contrast media source 12' (the remnant data value). At the same time, it monitors and tracks the cumulative amount of contrast medium that has been delivered to the patient (the dosage amount data value). A more detailed description of the functions provided by the digital processor 220 will be provided in connection with a description of the preferred method of the current system, set forth in Section II below.

Figure 3:
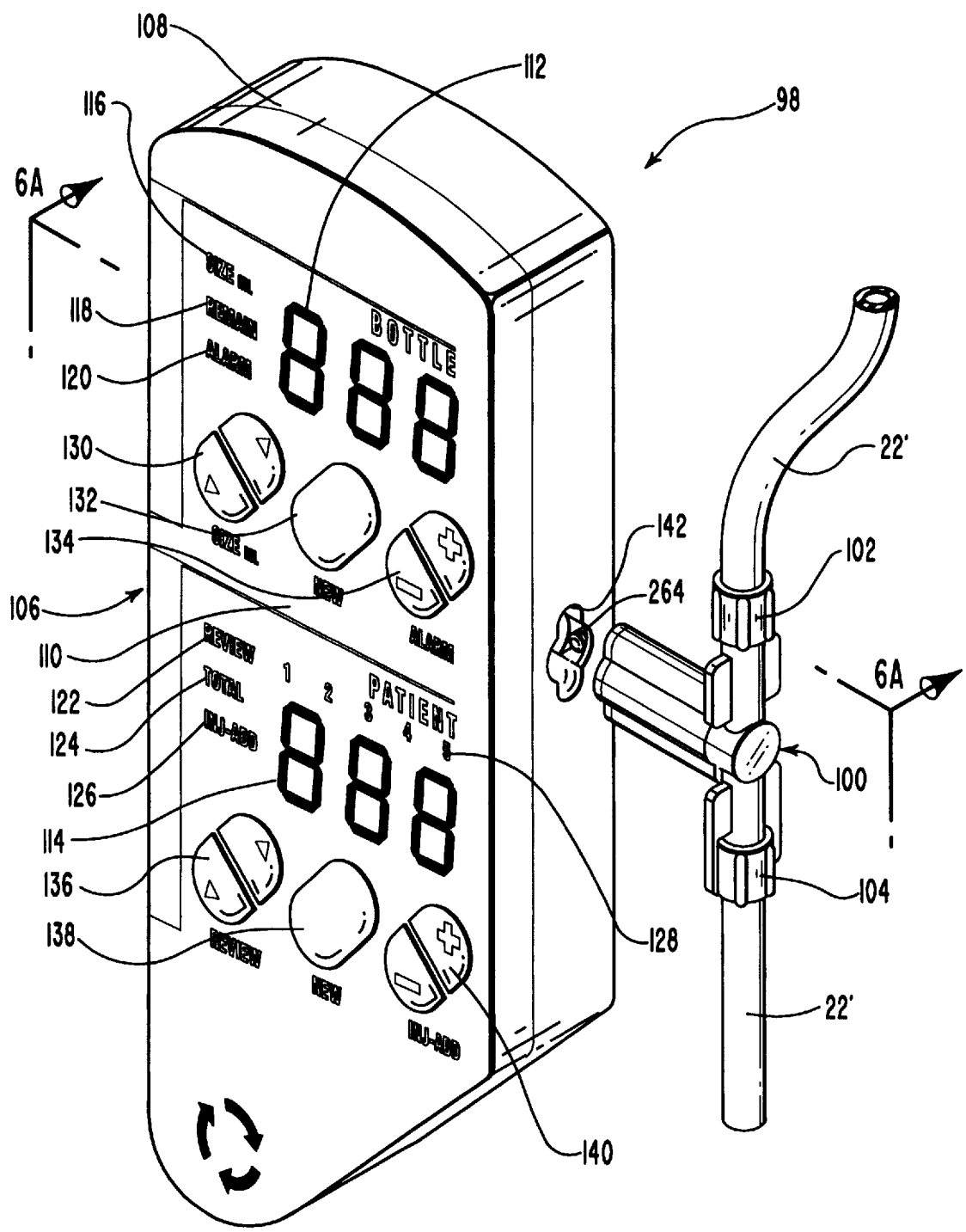
FIG. 3 is an enlarged perspective view illustrating the electronic controller and the flow indicator, along with associated tubing.

FIGS. 2 and 3 illustrate how the electronic controller 106 includes a front control panel 110. The display means of the system is shown in the illustrated embodiment as comprising, in addition to corresponding portions of electronic circuitry disposed within the electronic controller 106, a first digital readout 112 and a second digital readout 114, both of which are positioned on the front control panel 110.

The digital readouts 112, 114 are each shown in the illustrated embodiment as comprising a conventional LED or LCD alphanumeric display having three, or any other suitable number, of controllable display positions for outputting numbers or letters. The digital readout 112 corresponds to the display portion labeled "BOTTLE," which is used to display digital flow data relating to the amount of contrast medium that remains within the contrast media bag 12' (remnant data). The digital readout 114 corresponds to the display portion labeled "PATIENT," which is used to display digital flow data relating to the amount of contrast medium that has been administered to a patient (dosage amount data).

In the preferred embodiment, the control panel 110 includes a series of annunciators, each of which provides an indication to the system user of what is currently being displayed on the digital readouts 112, 114. For example, associated with the first digital readout 112 is a "SIZE" annunciator 116, a "REMAIN" annunciator, and an "ALARM" annunciator 120. Associated with the second digital readout 114 is a "REVIEW" annunciator 122, a "TOTAL" annunciator 124, a "INJ-ADD" annunciator 126, and a series of patient ID annunciators 128, shown here as the numerals one through five. Each annunciator is capable of being selectively illuminated, by way of corresponding circuitry contained within the electronic controller 106, so as to indicate to the system user what type of flow data is currently being displayed, or which of the optionally selectable functions are currently being carried out by the digital processor 220. The circumstances under which a particular annunciator is illuminated will be described more fully in Part II.

Also included within the preferred embodiment of the electronic controller 106 is switch means, disposed on the control panel 110, for allowing the system user to select which one of a number of different optional functions are to be performed by the digital processor 220. The switch means is shown in the illustrated embodiment as comprising, for example, a series of touch sensitive button switches along with the corresponding electronic circuitry disposed within the electronic controller 106. The button switches include a "SIZE" switch 130, a "NEW" switch 132, and an "ALARM" switch 134, each of which is positioned on the control panel 110 so as to be associated with the first digital readout 112; and a "REVIEW" switch 136, a "NEW" switch 138, and a "INJ-ADD" switch 140, each of which is positioned on the control panel 110 so as to be associated with the second digital readout 112. The exact function that is invoked upon actuation of each of these button switches will be more fully described in Part II, in connection with FIGS. 9A through 9C.

In a presently preferred embodiment, the monitoring system of the present invention also includes means for coupling the electronic controller 106 to the positive displacement device 100 in a detachable manner. Once the electronic controller 106 is coupled to the displacement device 100, and contrast medium fluid is dispensed to the patient, the digital processor 220 can begin processing the measured contrast media values so as to derive therefrom the digital flow data. Because the attachment is detachable, the positive displacement device 100 can be detached and then discarded (or re-sterilized) after each patient procedure. The electronic controller 106 can then be reused in another patient procedure by simply attaching it to a new displacement device 100—by way of the coupling means. Because a large portion of the overall system cost is associated with the electronics contained within the controller 106, this ability to reuse the controller 106 results in an extremely economical monitoring system.

FIG. 3 illustrates, by way of example, one preferred manner of implementing the coupling means. Formed in the side of the electronic controller 106, is a receptacle housing 142. The receptacle housing 142 is shaped so as to correspond with the dimensions of the outer periphery of the displacement device 100, and is sized such that the displacement device 100 can be received in a tight fitting, yet releasable manner. It will be appreciated that a variety of other attachment/detachment schemes could be utilized to provide this coupling function, including spring actuated clips or clamps. Also, the controller 106 need not necessarily be physically coupled directly to the sensor 100. For example, the coupling function could be accomplished via a connector and a detachable cable, including associated interface electronics, whereby the displacement device 100 is physically separated from the controller 106.

Figure 4:
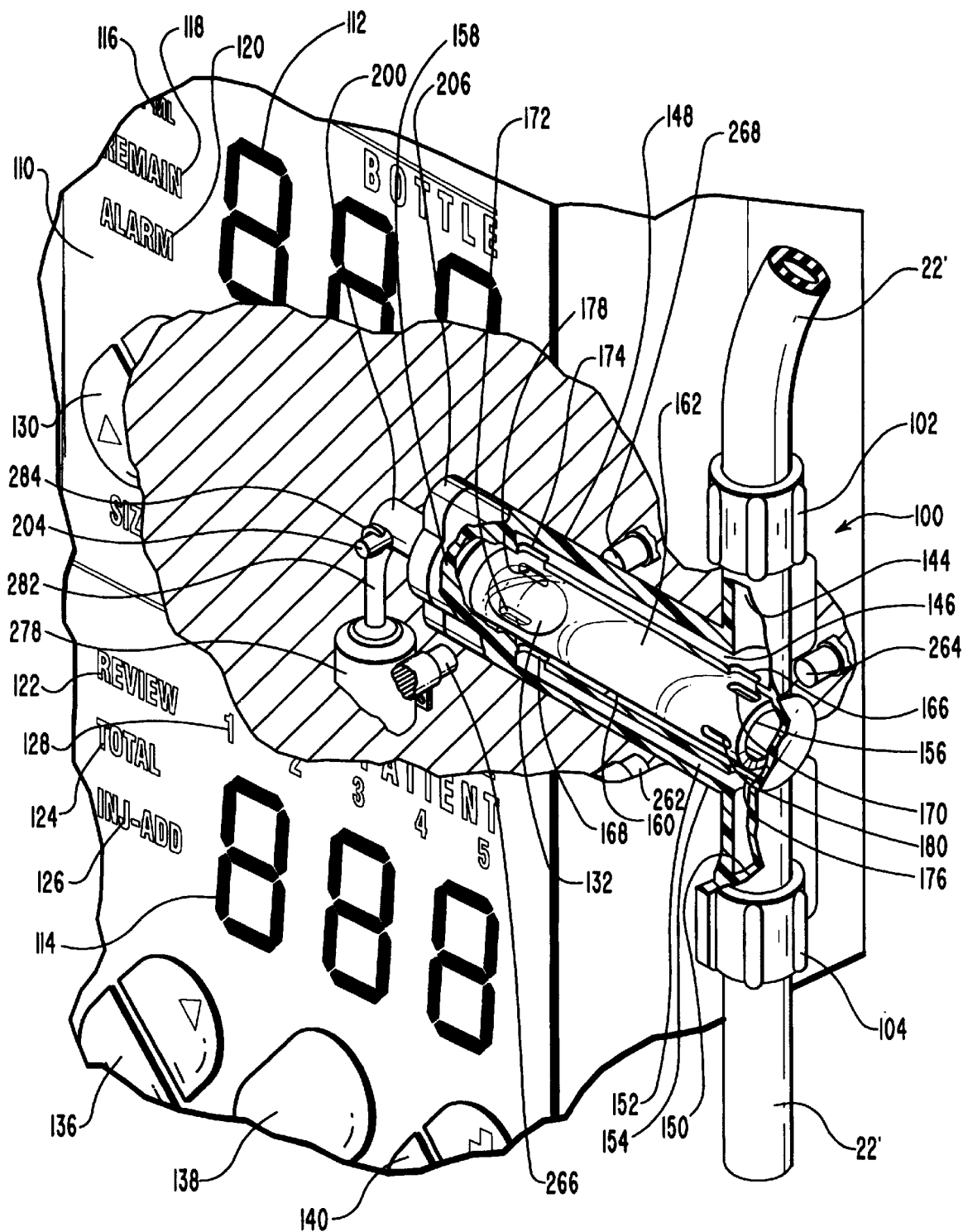
FIG. 4 is a cut-away view illustrating the flow indicator operatively coupled to the electronic controller.

Reference is next made to FIG. 4, which illustrates, by way of a cut-away view, the positive displacement device 100 operatively coupled to the electronic controller 106. As previously noted, the displacement device 100 measures the amount of contrast medium that is dispensed to the patient by providing an indication of the amount of fluid that is displaced through the device 100. The amount of fluid that is being displaced through the device 100 is provided to the digital processor 220, which then functions so as to derive the digital flow data.

The presently preferred structure and operation of the positive displacement device 100 will next be described by making particular reference to FIGS. 4 through 6 together. In the preferred embodiment, the positive displacement device 100 is comprised of an inlet chamber means for receiving the contrast medium from the fluid conduit, and an outlet chamber means for returning the contrast medium received at the inlet chamber means to the fluid conduit. As can best be seen in FIGS. 4 and 6, the inlet chamber means includes, for example, an inlet port 144, to which is connected standard Luer connector 102, which is detachably connected to the inlet line 22' at a point downstream from the contrast media bag 12'. In the preferred embodiment, the input chamber means also includes an inlet chamber 146, formed within an elongate housing 148 coextensively formed along the length of the displacement device 100. All fluid received at the input port 144 flows into inlet chamber 146.

In a similar fashion, the outlet chamber means includes an outlet port 150, to which is also connected a standard Luer connector 104. Connector 104 is in turn detachably connected to the inlet line 22' at a point downstream from the displacement device 100. The output chamber means also includes an outlet chamber 152, formed within an elongate outlet chamber housing 154 coextensively formed along the length of the displacement device 100 on a side opposite to the elongate housing 148. Outlet chamber 152 is in fluid communication with the outlet port 150, and all fluid received at the input port 144 will ultimately return to the inlet line 22' via outlet chamber 152, in the manner described below.

The displacement device 100 also includes a means for defining a main fluid chamber. As is shown in FIGS. 4 through 6, an intermediate housing 158 is disposed coextensively between the inlet chamber housing 148 and the outlet chamber housing 154. Intermediate housing 158 is cylindrical in shape, and is hollow so as to form an elongate cylindrical chamber 160. Received within the cylindrical chamber 160 is a fluid cylinder 162. The outer periphery of fluid cylinder 162 is cylindrical in shape, and is sized, both in terms of circumference and length, so as to fit coextensively within the cylindrical chamber 160 in a tight fitting, yet moveable manner. This is best illustrated in FIGS. 6A and 6B. In addition, the fluid cylinder 162 is hollow along substantially its entire length, thereby forming a main fluid chamber 164 having an interior surface 156.

The preferred embodiment of the positive displacement device 100 further comprises a valve means for selectively defining either a first fluid communication path, or a separate, second fluid communication path. The first and the second fluid communication paths each provide a separate path of fluid communication between the inlet chamber 146, the main fluid chamber 164, and the outlet chamber 152.

Figure 5:
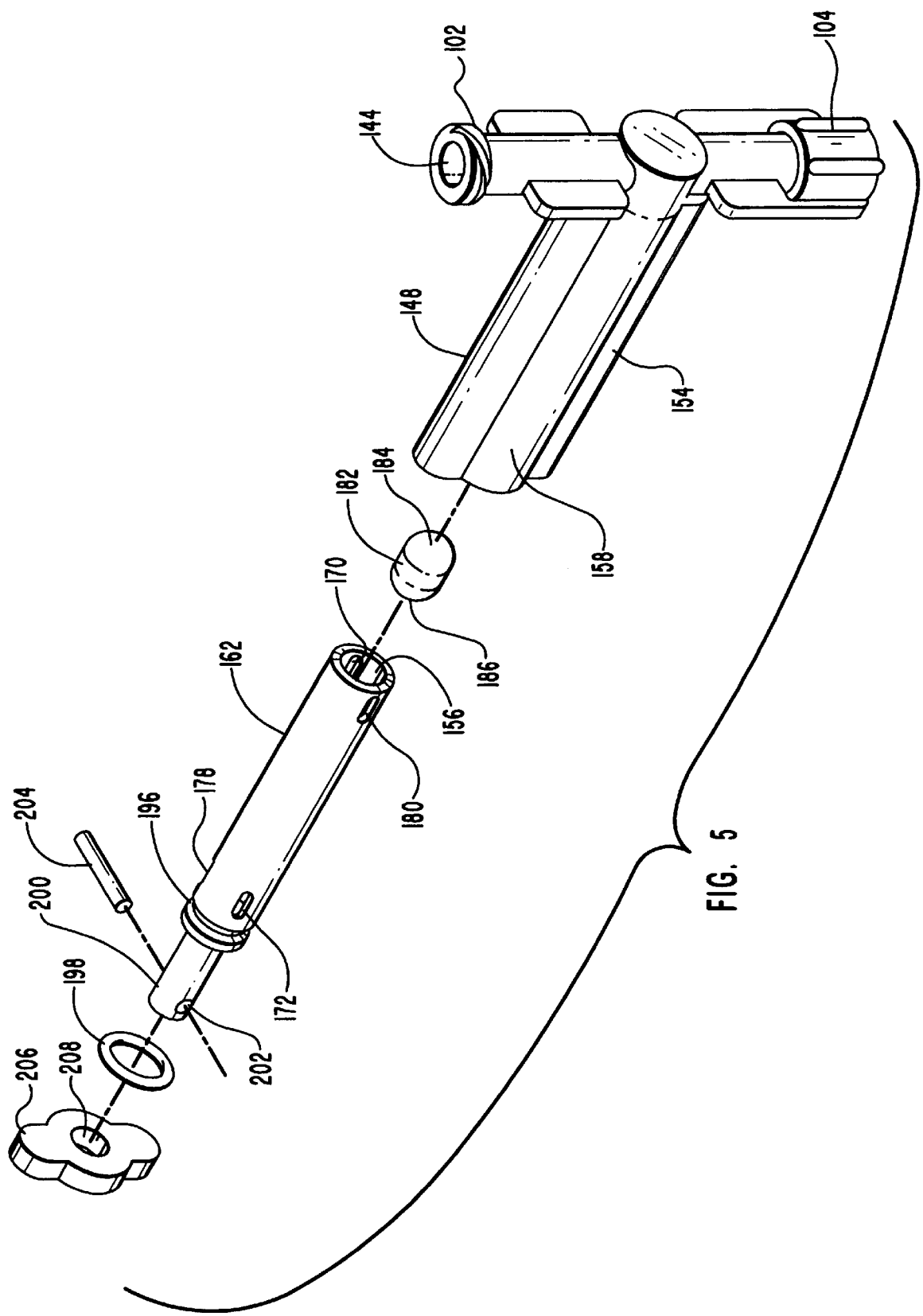
FIG. 5 is an exploded perspective view of the flow indicator.
Figure 6A:
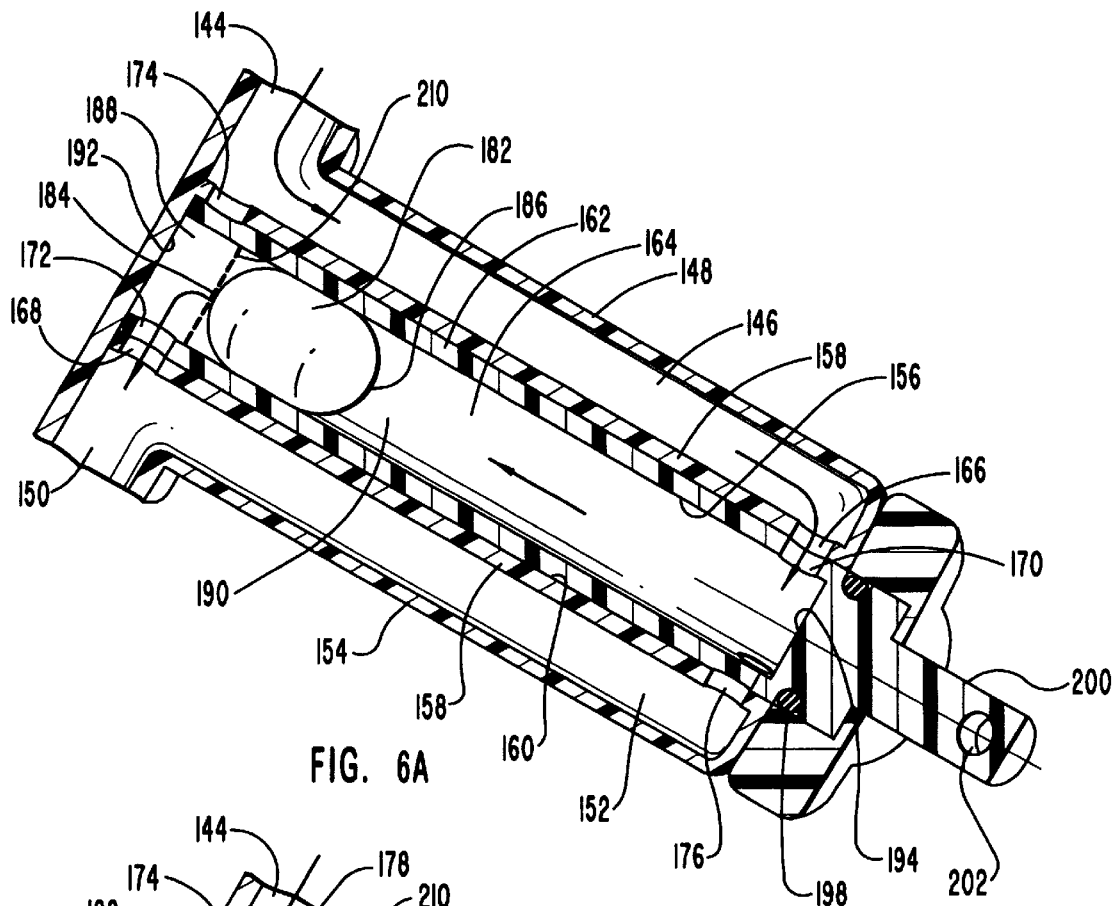
FIGS. 6A and 6B are both cross-sectional views of the flow indicator taken along lines 6A—6A in FIG. 3, illustrating each of the preferred valve positions, and the resultant fluid flow and internal operation of the flow indicator.
Figure 6B:
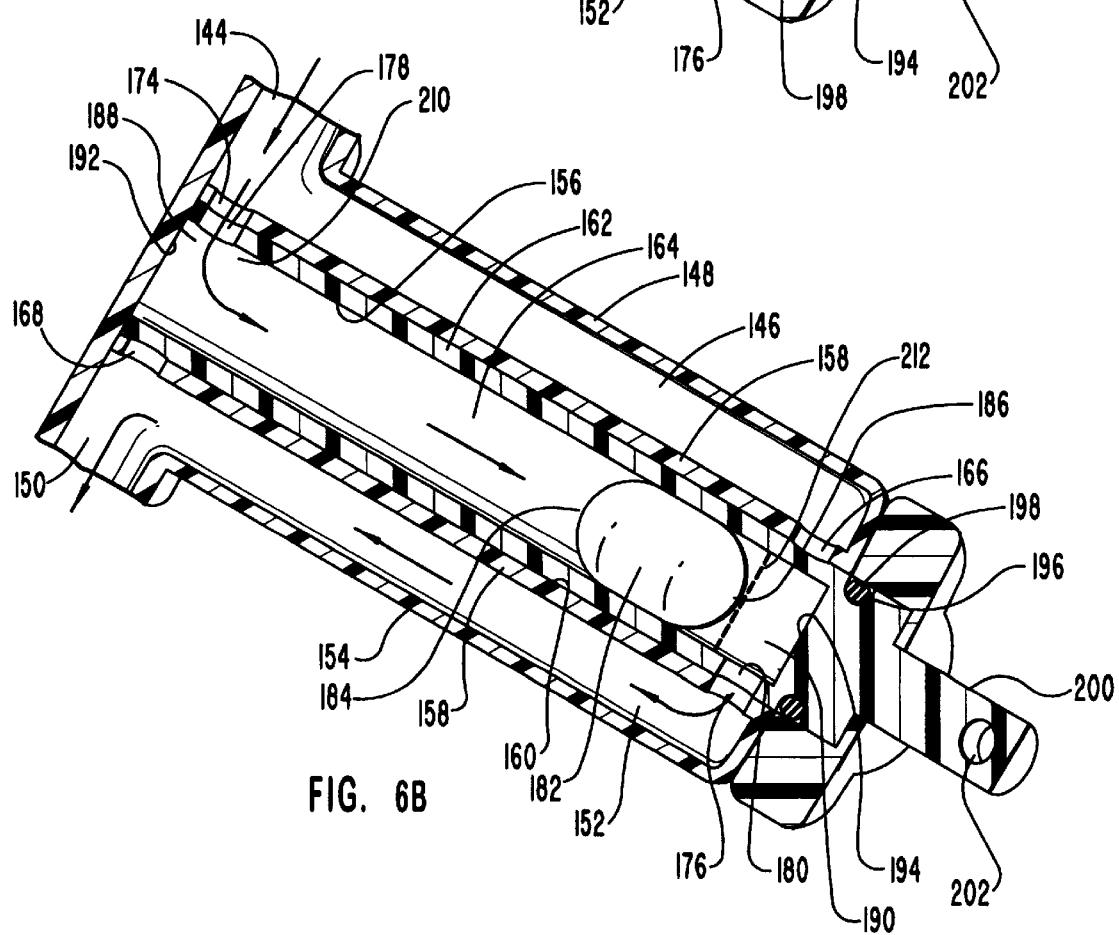

FIGS. 4 through 6 illustrate one preferred structure for implementing the valve means. In the preferred embodiment, the valve means is comprised of a first valve position, which defines the first communication path, and a second valve position, which defines the second communication path. The first valve position, best shown in FIG. 6A, is formed by a first pair of valve apertures 166, 168, and a second pair of valve apertures 170, 172. The first pair of apertures 166, 168 are formed through the intermediate housing 158 at opposite ends, with aperture 166 forming a fluid path with the inlet chamber 146, and aperture 168 forming a fluid path with the outlet chamber 152. The second pair of valve apertures 170, 172 are formed through the fluid cylinder 162 at opposite ends, each of which form a fluid path with the main fluid chamber 164. When the displacement device 100 is positioned in this first valve position, apertures 166 and 170 are aligned, and apertures 168 and 172 are aligned, so as to define the first fluid communication path between the inlet chamber 146, the main fluid chamber 164, and the outlet chamber 152. This path is designated by way of the flow arrows in FIG. 6A.

Similarly, the second valve position, which is best shown in FIG. 6B, is formed by a first pair of valve apertures 174, 176, and a second pair of valve apertures 178, 180. The first pair of apertures 174, 176 are formed through the intermediate housing 158 at opposite ends with aperture 176 forming a fluid path with the outlet chamber 152, and aperture 174 forming a fluid path with the inlet chamber 146. The second pair of valve apertures 178, 180 are formed through the fluid cylinder 162 at opposite ends, each of which form a fluid path with the main fluid chamber 164. When positioned in this second valve position, apertures 174 and 178 are aligned, and apertures 176 and 180 are aligned, so as to defined the second communication path between the inlet chamber 146, the main fluid chamber 164, and the outlet chamber 152. This path is designated by way of the flow arrows in FIG. 6B.

Due to the orientation of the first and second series of valve apertures, a change from a first valve position (FIG. 6A) to a second valve position (FIG. 6B), or vice-versa, can be accomplished by merely reorienting the fluid cylinder 162 within the cylindrical chamber 160. In the preferred embodiment, this reorientation is accomplished by rotating the fluid cylinder 162 within the cylindrical chamber 160, in a manner described below. Alternatively, the valve apertures could be oriented relative to one another such that the valve change could be accomplished by sliding the fluid cylinder 162 within the cylindrical chamber 160.

The positive displacement device 100 is further comprised of a displacement indicator means, which is disposed within the main fluid chamber 164 so as to be moveable in response to a fluid pressure within the displacement device 100. Thus, the displacement indicator means functions so as to indicate the delivery of a predetermined measured volume of contrast medium through the outlet chamber 152 via the first communication path (FIG. 6A) when it has been displaced to a first indicator position, or via the second communication path (FIG. 6B) when it has been displaced to a second indicator position.

FIGS. 4 through 6 illustrate one preferred example of displacement indicator means as comprising a fluid displacement indicator 182, having a first 184 and a second 186 end. The displacement indicator 182 is shaped so as to fit within the main fluid chamber 164 in a tight fitting manner, yet it is moveable within the chamber 164 when a fluid pressure is applied to either of the first 184 or second 186 ends. Movement of the indicator 182 can result from a negative or a positive pressure, created within the inlet line 22'. Further, the indicator 182 is sized and constructed from a suitable material, so that its outer periphery forms a fluid-tight fit with the interior surface 156 of the chamber 164.

As is best seen in FIGS. 6A and 6B, when placed within the main fluid chamber 164, the indicator 182 essentially divides the chamber 164 into first 188 and second 190 reservoirs, both of which are separated from one another in a fluid-tight manner by the indicator 182. As long as the valve is in one of the two open positions (FIG. 6A or FIG. 6B), the indicator 182 can be displaced within the main fluid chamber 164 and thereby allow each reservoir to vary in volume, i.e., as one gets larger, the other gets smaller. As the indicator 182 is displaced towards one or the other ends of the chamber 164 (designated as the first 192 and second 194 interior surface ends), the fluid contents of the reservoir corresponding to that particular interior surface end is displaced out the outlet port 150 via the outlet chamber 152, and the reservoir corresponding to the opposite end of the indicator 182 is filled with a corresponding amount. The volume amount that has been dispensed from one reservoir, and introduced to the opposite reservoir at any given time, can be derived from the relative position of the indicator 182 within the main fluid chamber 164 at that given time. It is in this way that the positive displacement device 100 provides an indication as to the amount of contrast medium displaced through the device.

In operation, the contrast medium is delivered to a patient by creating a fluid pressure within the inlet line 22', typically by way of the syringe plunger 50'. Assuming that the valve is in the first valve position, shown in FIG. 6A, contrast medium will flow through the inlet port 144, into inlet chamber 146 and into the main fluid chamber 164 via the first fluid communication path, as is indicated by the flow arrows. The second reservoir 190 will fill with fluid and pressure created by the syringe plunger 50' will cause the displacement indicator 182 to be displaced towards the first interior surface end 192 of the main fluid chamber 164, as is shown in FIG. 6A. The contents of the first reservoir 188 are simultaneously displaced from within the main fluid chamber 164, into the outlet chamber 152, through the outlet port 150 and back into inlet line 22' towards the patient. At the same time, the second reservoir 190 is filled with a corresponding volume of fluid via the inlet chamber 146.

If the indicator is displaced to the point where it abuts against the interior surface end 192, the size and shape of the fluid indicator 182 will cause the first fluid communication path to be closed off. Thus, for the administration of the contrast medium to continue, the valve means must be manipulated so as to be placed in the second valve position, thereby defining the second fluid communication path, shown in FIG. 6B. As discussed above, this is done by rotating the fluid cylinder 162 within the intermediate housing 158. When in the second valve position, contrast medium will then continue to flow through the displacement device 100, flowing through the inlet port 144, into inlet chamber 146 and into the main fluid chamber 164 via the second fluid communication path, as is indicated by the flow arrows. The first reservoir 188 will fill with fluid and pressure created by the syringe plunger 50' will cause the displacement indicator 182 to be displaced towards the second interior surface end 194 of the main fluid chamber 164, as is shown in FIG. 6B. The contents of the second reservoir 190 are simultaneously displaced from within the main fluid chamber 164, into the outlet chamber 152, through the outlet port 150 and back into inlet line 22' towards the patient, and the first reservoir 188 is filled with a corresponding volume of fluid via the inlet chamber 146.

In either valve position, the relative position of the displacement indicator 182 within the main fluid chamber 164 provides an indication of the volume of contrast medium that has been dispensed through the displacement device 100. Preferably, an "indicator" position within the main fluid chamber 164 is selected for each valve position. In the first valve position, a "first indicator position" is selected, designated by the dotted line at 210, which corresponds to a fixed volume of fluid being displaced from the first reservoir 188 when the first end 184 of indicator 182 has reached this position. Similarly, for the second valve position, a "second indicator position" is selected, designated by the dotted line at 212, which corresponds to a fixed volume of fluid being displaced from the second reservoir 190 when the second end 186 of the indicator has reached this position. In the preferred embodiment, displacement of the indicator 182 to either of these "indicator positions" not only denotes that a fixed amount of fluid has been dispensed, it also signals that the displacement device 100 should be changed to the next valve position so as to permit continued fluid flow through the device 100. In the preferred embodiment, displacement of the indicator 182 to either of the indicator positions 210, 212 indicates that 0.4 milliliters of fluid have been displaced. It will be appreciated that the selection of different indicator positions would result in a different fixed volume being displaced.

Whenever the displacement indicator 182 is displaced within the main fluid chamber 164 to the point where it abuts against the first or second interior surface ends 192, 194, the corresponding fluid communication path is completely closed off. This of course causes a discontinuity in the flow of contrast medium through the displacement device 100, at least until the device 100 can be changed to the next valve position. Such an interruption in flow is undesirable, and since the change from one valve position to the next cannot happen instantaneously, the valve change should be initiated before the fluid communication path is completely closed off. This assures that there is a continuously open path of fluid communication through the displacement device 100. Thus, in the preferred embodiment the first and second indicator positions at 210, 212 are selected such that the first or second fluid communication paths through the displacement device 100 are never completely closed off. It will be appreciated that this is merely an implementation choice, and in some situations it may be desirable to allow the indicator 182 to completely close off the fluid communication paths before switching to the next valve position.

FIG. 5 illustrates certain other aspects of the positive displacement device 100. Formed around the outer periphery of the fluid cylinder 162 is an O-ring retention groove 196, which receives rubber or silicone O-ring 198. O-ring 198 assures a fluid-tight fit when the cylinder 162 is received within the cylindrical chamber 160 of intermediate housing 158, while at the same time, lending lubricity so as to permit easier rotation of cylinder 162 within housing 158. Extending from the distal end of fluid cylinder 162 is an actuation arm 200, which in turn has formed through it a bore 202 that receives a lever arm 204. The lever arm 204 provides a means by which the fluid cylinder 162 can be rotated within the intermediate housing 158 so as to operate the valve means, in a manner which will be described in further detail below. An end enclosure 206 is placed over the actuation arm 200, via enclosure hole 208, so as to abut against the distal ends of the inlet chamber 148, intermediate 158, and outlet chamber 154 housings. The outer periphery of this end enclosure corresponds in shape and size to the outer periphery formed by the housings 148, 158, 154, thereby allowing for easier insertion, retention and support of the displacement device 100 within the receptacle housing 142.

To summarize, while a number of different types of flow sensors could be used to provide the function of the flow indicator means of the present invention, the positive displacement device 100 is advantageous in several respects. The device 100 provides an accurate indication of the amount of contrast medium administered to a patient based on the amount of medium that is displaced through the device 100. As such, the device 100 is accurate regardless of the viscosity, temperature and/or other flow characteristics of the fluent medium being administered. Further, the device 100 is comprised of few moving parts, and can be economically manufactured using standard injection molding techniques. Because the positive displacement device 100 has a low per-unit cost, it can be discarded after each use, thereby avoiding expensive and time-consuming resterilization. This low cost also contributes to the overall low cost of the electronic monitoring system.

The discussion will next turn to a description of one presently preferred embodiment of the electronic controller 106 aspect of the invention. As previously noted, the electronic controller 106 includes digital processor means. The digital processor means functions so as to receive the measured amount of contrast medium dispensed through the fluid conduit, as indicated by the flow indicator means, and then processes that amount value so as to electronically monitor, display and record digital flow data. This digital flow data can include, for example, remnant data, which represents the amount of contrast medium that remains within the contrast media bag 10', and dosage amount data, which represents the amount of contrast medium that has been delivered to the patient. The electronic controller 106 also includes data memory means for storing the digital flow data for later retrieval and output, and program memory means for storing the machine-readable instructions that are used by the digital processor means to electronically derive the digital flow data.

Figure 7:
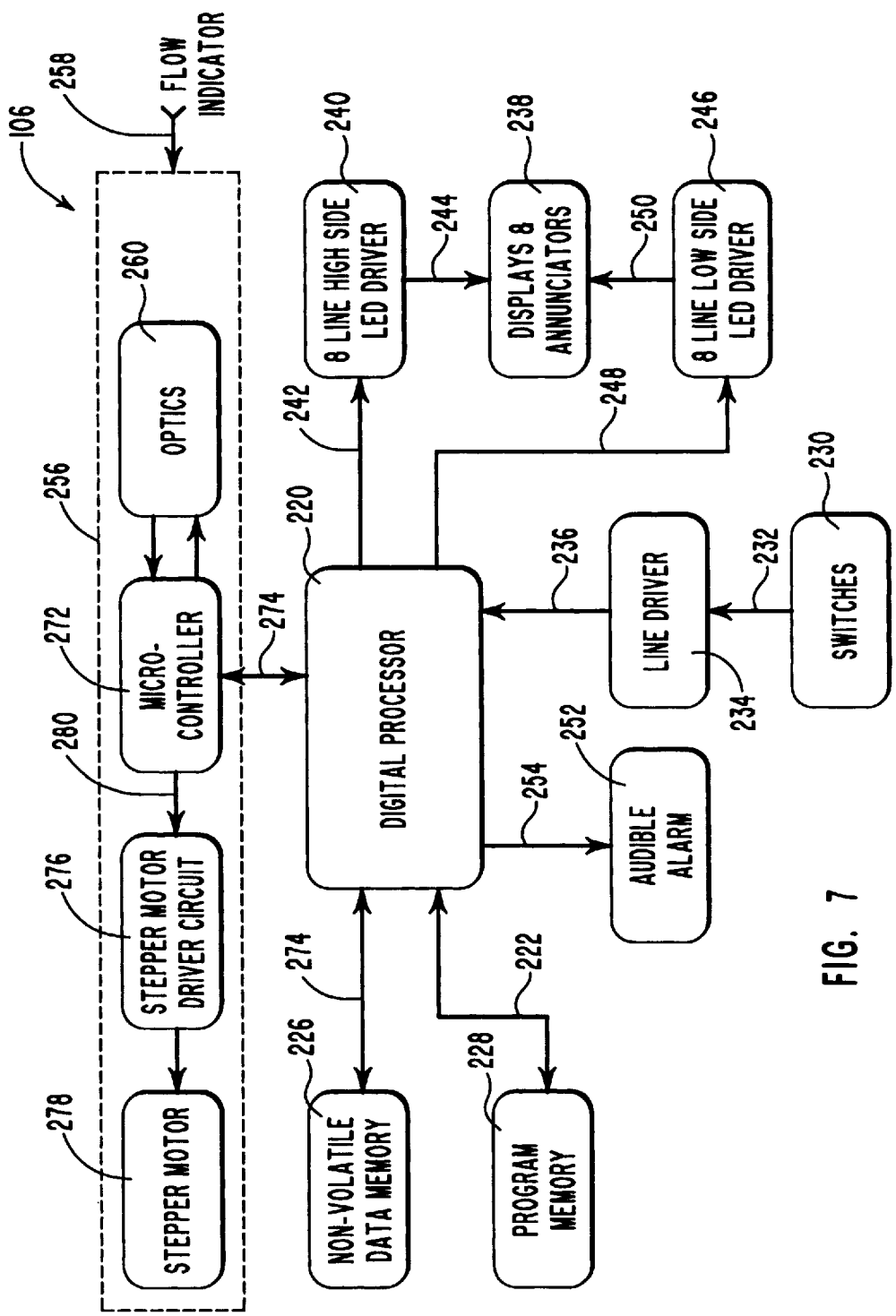
FIG. 7 is a functional block diagram that schematically illustrates the primary functional components used in one presently preferred embodiment of the electronic circuitry used in connection with the electronic controller.

Reference is next made to FIG. 7, where one example of the electronic controller means of the system is more particularly illustrated. The digital processor means is comprised of a programmable digital processor 220, which could be any one of a number of currently available programmable microprocessors of the 8 or 16-bit variety. The digital processor 220 is interfaced, by way of a standard address and data bus scheme as is shown schematically at line 222, with program memory means, such as program memory 228. In the preferred embodiment, program memory 228 is comprised of any suitable read-only memory storage device having sufficient capacity for holding the program instructions used by the digital processor 220. In the preferred embodiment, an EEPROM device or devices is used, so as to permit subsequent updates or changes to the program instructions. Also interfaced with the digital processor 220 by way of the internal data and address bus, shown schematically at line 224, is a non-volatile memory 226 device, which provides the function of the data memory means. While this memory function could be provided by a variety of different memory devices, it is preferably accomplished with a suitable arrangement of battery-backed RAM, capable of at least 1K bytes of storage. The memory should have power-down protection, such that data is preserved in the event of an unscheduled power loss.

The digital processor 220 is also interfaced with the display means and the switch means discussed above. Thus, in the preferred embodiment, the series of touch sensitive button switches, represented in FIG. 7 at functional box 230, and positioned on the control panel 110 of the electronic controller 106, are electronically interfaced with the digital processor 220 by way of standard interface circuitry, shown as a line driver circuit 234, and schematic lines 232 and 236. In this way, when a particular switch is actuated, it is detected by the digital processor 220 and then processed in the appropriate manner, as is described in more detail in Section II.

In a similar fashion, the digital processor 220 is interfaced with the display means, which in the illustrated embodiment is comprised of first digital readout 112, second digital readout 114, and the various annunciators positioned on the front control panel 110 (FIG. 3), and which are collectively represented in FIG. 7 at functional box 238. In the preferred embodiment, the first digital readout 112 and its associated annunciators, described above in connection with FIG. 3, are interfaced with the digital processor 220 by way of a standard LED driver circuit 240 and schematic lines 242 and 244. Similarly, the second digital readout 114 and its associated annunciators are controlled by the digital processor 220 via the interface represented by the second LED driver circuit 246 and schematic lines 248 and 250.

An additional aspect of the preferred embodiment of the electronic controller 106 is an alarm means. This alarm means provides the function of alerting the system user—by outputting some type of alarm indicator—when the amount of contrast medium that remains within the contrast medium source bag 10' ( referred to as the remnant data value) falls below a certain predefined level (which can be specified by the user, as discussed in further detail below in connection with FIGS. 9A through 9C). In this way, the electronic controller 106 provides a means by which the user will be notified when the medium bag 10' needs to be replaced, thereby insuring the patient's safety, in a way such that the system user does not have to continuously visually monitor the contents of the bag 10'. This adds to the overall ease-of-use and safety of the system.

By way of example and not limitation, the alarm means is implemented with an audible alarm circuit, shown at 252 in FIG. 7. Preferably, this audible alarm circuit 252 is comprised of some type of audio output device, such as a piezo-electric element, that is capable of microprocessor-derived frequencies at or about 2 KHz. Thus, when the amount remaining within the source bag 10' falls below a specified level, the digital processor 220 will cause the alarm to sound, via schematic line 254.

Also included within the preferred embodiment of the electronic controller 106 is a sensor means. The sensor means functions so as to operatively interface the electronic controller 106 with the positive displacement device 100. This operative interface must be such that the electronic controller 106 is able to detect the amount of contrast medium that is dispensed through the inlet line 22', and in a manner such that the positive displacement device 100 is appropriately manipulated so as to function correctly. In the preferred embodiment the indicated amount is detected by sensing by the relative position of the displacement indicator 182 within main fluid chamber 164, and operation of the displacement device 100 involves primarily switching it between the two valve positions at the appropriate times. Of course, if a different fluid flow indicator means were used, this operative interface would be varied accordingly. In addition, the sensor means also functions so as to generate an "electrical flow signal," which is representative of the amount of contrast measured and indicated by the displacement device 100. This electrical flow signal can then be supplied to the digital processing means for further processing and derivation of the digital flow data.

In the preferred embodiment, the sensor means includes means for providing a displacement signal when the displacement indicator 182 is displaced to the first indicator position, or to the second indicator position (designated at dotted lines 210, 212 in FIGS. 6A and 6B). As noted above, movement of the indicator 182 to the first (or second) indicator position denotes that a fixed volume of contrast medium has been displaced through the device 100. Thus, each time the displacement signal is generated indicates that a fixed volume of fluid has been displaced through the device 100, which in the preferred embodiment is 0.4 milliliters.

Also included within the sensor means is a valve operation means that is responsive to this displacement signal in a manner such that the valve means is appropriately operated between the first valve position (defining the first fluid communication path—FIG. 6A) and the second valve position (defining the second fluid communication path—FIG. 6B). This insures that one of the two fluid communication paths are always open, allowing for continued administration of the contrast medium.

In the preferred embodiment, the sensor means also includes a controller means. The controller means monitors the status of the displacement signal, and generates in response to that signal the "electrical flow signal" that is representative of the amount of medium dispensed through the displacement device 100. This amount is based primarily upon the fixed volume dispensed from the first or second reservoirs 188, 190 when indicator 182 is displaced to the first or second indicator positions, but also includes a "correction" amount, as will be discussed in Part II below in connection with FIG. 8.

FIG. 7 illustrates, by way of example and not limitation, one preferred embodiment of the sensor means as comprising a sensor circuit, which includes the functional components within the dotted box 256. When the electronic controller 106 is detachably coupled to the displacement device 100, as is represented schematically at line 258, the sensor circuit 256 is operatively interfaced with the displacement device 100 so as to be able to continuously detect the amount of contrast medium that is dispensed through the device 100. While other detection techniques could be employed, in the preferred embodiment the function is accomplished optically with optics circuit 260. Optics circuit 260 is configured to monitor the relative position of the displacement indicator 182 within the main fluid chamber 164, and includes a pair of optical emitters and detectors, the relative positioning of which are best seen in FIG. 4. As is shown there, a first optical emitter 262 and detector 264 pair are positioned relative to the displacement device 100 so as to be able to detect when the first end 184 of the displacement indicator 182 has moved to the first indicator position (shown at 210 in FIG. 6A). Similarly, a second optical emitter 266 and detector 268 are positioned so as to be able to detect when the second end 186 displacement indicator 182 has moved to the second indicator position (shown at 212 in FIG. 6B). In this arrangement, at least the intermediate housing 158 and the fluid cylinder 162 portions of the displacement device 100 are constructed of a transparent material, such as a clear, medical grade plastic material. The displacement indicator 182 is constructed of an opaque material, so as to be capable of breaking the light beam generated by the optical emitters 262, 266. Thus, when the light signal emitted by either of the emitters 262, 266 is broken, and detected by the corresponding detector 264, 268, an electrical "displacement signal" pulse is generated, thereby indicating that the indicator 182 has been displaced to either of the indicator positions.

Referring again to FIG. 7, the displacement signal is supplied, as is shown schematically at line 270, to a microcontroller 272, which provides the function of the controller means portion of the sensor circuit 256. Microcontroller 272 includes any suitable programmable device, such as a standard eight-bit microcontroller, available from any one of a number of manufacturers. Also included in addition to microcontroller 272 are standard interface and control circuitry for interfacing with optics circuit 260, and storage means for storing the program instructions used by the programmable microcontroller. This program instruction means function could be provided by a separate, read only memory type device, such as an EEPROM—as is done in the preferred embodiment—or it could implemented by permitting the microcontroller 272 to share an appropriate portion of the address space provided by program memory 228. This could be done by way of a standard address and data bus arbitration scheme.

As will be discussed in further detail in Part II below, the microcontroller 272 programmably monitors the status of the displacement signal and, when detected, derives and outputs an electrical flow signal, as is schematically shown at line 274. This electrical flow signal represents the amount of contrast medium that has been dispensed through the line 22', as is indicated by the displacement device 100.

While in the preferred embodiment, the controller means portion of the sensor means is implemented by way of a separate, programmable device (microcontroller 272), it will be appreciated that the function could be implemented via suitable, hardwired logic components. Alternatively, the function could also be provided by the digital processor 220 itself, provided that the processor 220 is a device capable of sufficient processing speeds.

Also included in sensor circuit 256 is a standard stepper motor driver circuit 276, which interfaces with and controls the operation of a miniature stepper motor 278. Driver circuit 276 and motor 278 together provide the function of the valve operation means, by operating the valve portion of the displacement device 100 between the first valve position (first fluid communication path—FIG. 6A) and the second valve position (second fluid communication path—FIG. 6B). This aspect of the interface assures that the displacement device 100 can be operated in substantially real time, and thereby continuously monitor the administration of the contrast medium.

As is shown in FIG. 7, the stepper motor driver circuit 276 is interfaced with the microcontroller 272 at schematic line 280. The microcontroller 272, upon receipt of the displacement signal, outputs an appropriate control signal to the driver circuit 276, which in turn causes the stepper motor 278 to actuate a motor arm 282. This motor arm 282, best seen in FIG. 4, is in turn coupled to the lever arm 204, which is connected to the actuation arm 200 portion of the fluid cylinder 162. Upward and/or downward movement of the motor arm 282 for a predefined distance results in a rotational movement of the fluid cylinder 162, thereby moving the displacement device 100 into the next valve position. Thus, when the displacement indicator moves to the first or second indicator positions, the driver circuit and motor 276, 278 combination respond to the resulting displacement signal (by way of the microcontroller 272) by moving the displacement device 100 to the next valve position, thereby maintaining a continuously open fluid communication path.

As previously discussed, in the preferred embodiment the displacement device 100 is detachably connected to the electronic controller 106. As such, the motor arm 282 must be capable of connecting to the lever arm 204 in a detachable manner. As is best seen in FIG. 4, in the current embodiment this is done by including a C-shaped clip 284, having its open portion facing the lever arm 204. The lever arm 204 portion of the displacement device 100 can thus be detachably coupled to the electronic controller 106 by being received within this clip 284. Other detachable connection schemes could also be utilized.

Although not shown in FIG. 7, the presently preferred electronic controller circuit 106 also includes a means for supplying power to the circuit's various electrical components. Preferably, this power supply function is accomplished by way of a rechargeable battery (not shown), which enhances the controller's 106 overall portability and reusability. Further, the battery provides the ability to retain all data in the event that the controller 106 is powered off—intentionally or unintentionally. The controller circuit may also include a watch-dog supervisory circuit (not shown) that is capable of issuing an interrupt when a predefined timeout occurs. Such a timeout could be used, for instance, to power down the display, or the entire system, if there is no activity for a predetermined amount of time, thereby saving overall battery power. Of course, other power supply schemes could be used, including a conventional AC power supply arrangement, wherein power is obtained from an AC outlet.

In sum, the electronic controller portion of the system utilizes state-of-the-art electronics so as to be portable, reusable and easy to operate. Because it easily and detachably interfaces with the flow sensor indicator, the controller is very economical. At the same time, the controller provides the clinician with a variety of pertinent flow data in real time, thereby assuring the safe and efficient administration of parenteral fluid to the patient.

II. THE METHOD

Attention is next turned to a detailed description of the presently preferred program method by which the system of the present invention is used to continuously monitor, display and record flow data pertaining to the delivery of a contrast medium to a patient. The method is described by particularly referencing FIG. 8, which illustrates one presently preferred embodiment of the program instructions that can be used to control the microcontroller 272, and FIGS. 9A–9C, which illustrate one presently preferred embodiment of the program instructions which can be utilized to control the digital processor 220. As will be appreciated by those of ordinary skill in the art, and as noted above, while the system and method as described in reference to the preferred embodiments herein illustrate the system and method as implemented using state-of-the-art digital processing design and corresponding program instructions for controlling the microcontroller 272 and the digital processor 220, the system and method could also be implemented and carried out using a hard-wired design that accomplishes the necessary electronic processing. Such a design is also intended to be embraced within the scope of various of the claims as set forth hereafter.

Figure 8:
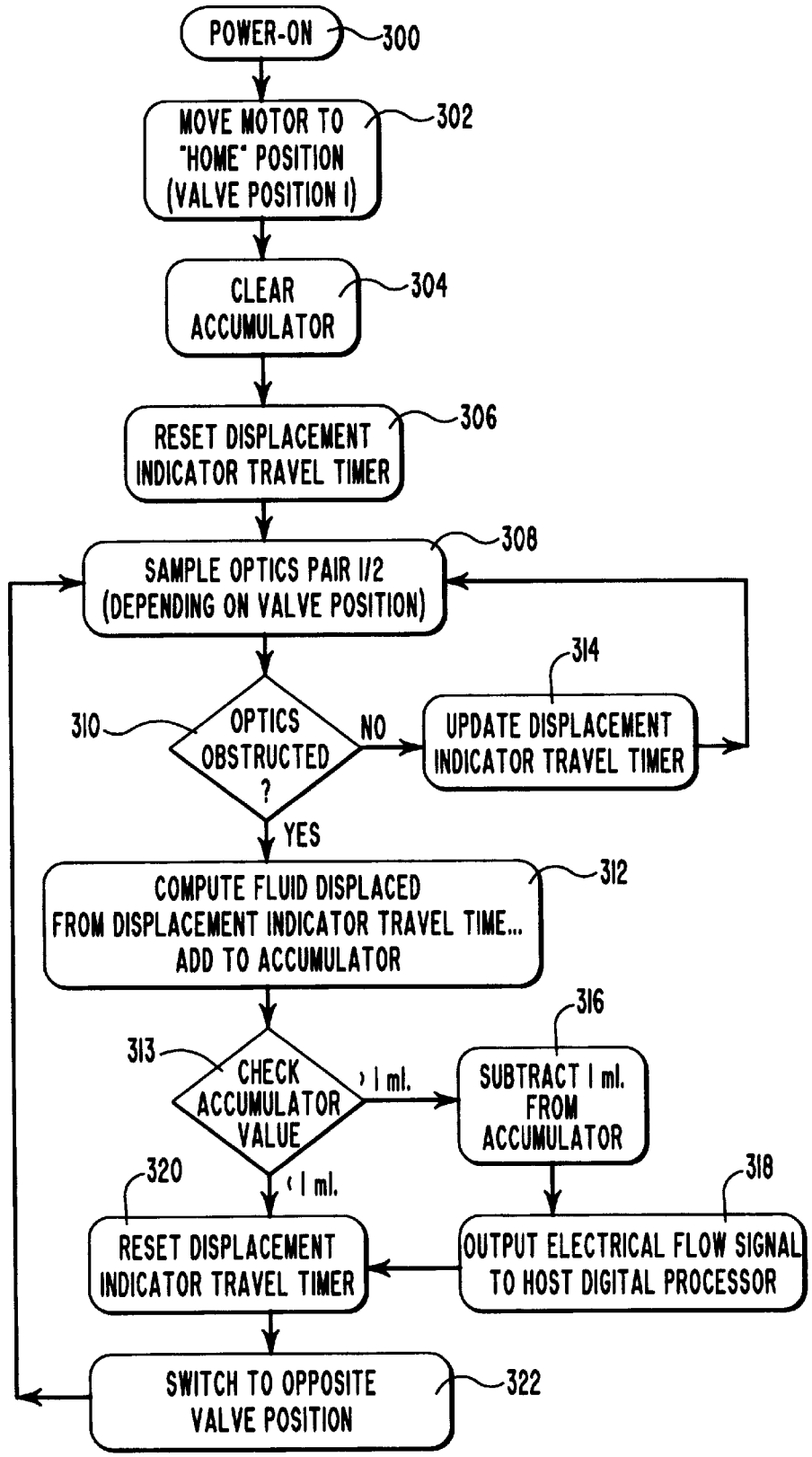
FIG. 8 illustrates a flow diagram that shows one presently preferred method for programming the microcontroller used in the sensor circuit portion of the electronic controller circuit of FIG. 7.

FIG. 8 illustrates a flow chart of the functional steps used to implement the program instructions for controlling the microcontroller 272 (shown functionally in FIG. 7). As discussed above, the microcontroller 272 is that portion of the sensor circuit 256 which monitors the displacement signal provided by the optics circuit 260 and which then generates the electrical flow signal that is representative of the amount of contrast medium flowing through the positive displacement device 100. This electrical flow signal is then provided to the digital processor 220 portion of the electronic controller 106.

When the electronic controller 106 is first powered on, the programmable microcontroller 272 begins at step 300 and performs various system initialization procedures. Also, at this step, the appropriate program instructions are loaded from the program memory used by the microcontroller 272. Following initialization, the microcontroller 272 moves to program step 302. At this step, the microcontroller 272 outputs a predetermined control signal to the stepper motor driver circuit 276 that will cause the stepper motor to place the positive displacement device 100 into the first valve position (FIG. 6A), otherwise referred to as the "home position."

Next, the microcontroller 272 proceeds to program step 304, where it clears the "accumulator" variable. As will be discussed in further detail below, the accumulator variable is used as temporary storage for keeping track of the volume of contrast medium that has been dispensed through the displacement device 100.

Next, the microcontroller 272 moves to program step 306. There, a timer referred to as the "Displacement Indicator Travel Timer" is reset to zero. This variable is used to keep track of the elapsed time that it takes the displacement indicator 182 to move between the two emitter/detector pairs 262, 264 and 266, 268 (FIG. 4).

After resetting the Displacement Indicator Travel Timer, the microcontroller 272 enters a program loop and begins sampling the appropriate emitter/detector pair 262, 264 or 266, 268, depending on what the current valve position is. This functional step is represented at box 308. The first time through this loop, the displacement device 100 is in the first valve position, and microcontroller 272 will sample the status of the first emitter 262 and first detector 264 pair. When the displacement device 100 is placed in the second valve position, the microcontroller 272 will sample the second emitter 266 and second detector 268 optics pair.

Microcontroller 272 next proceeds to program step 310, where it makes a decision based on the results of the previous program step 308. If the optics pair sampled at step 308 is obstructed, i.e., the displacement indicator 182 has been displaced within the fluid cylinder 162 to the first indicator position (or the second indicator position if the valve is in the second position) and thereby broken the light emitted by the first emitter 262, then the microcontroller 272 proceeds directly to program step 312. If, however, the optics pair has not yet been obstructed i.e., the displacement indicator has not yet reached the indicator position, then microcontroller 272 proceeds to program step 314.

At program step 314, the microcontroller 272 updates the Displacement Indicator Travel Timer, so as to keep track of the elapsed time that it takes for the displacement indicator 182 to travel between indicator positions. After updating the Travel Timer variable at step 314, the microcontroller 272 then returns to program step 308, where it continues to sample the status of the current emitter/detector optics pair. The microcontroller 272 will continue in this program loop (program steps 308, 310 and 314) until such time that at program step 310, it is determined that the current optics pair has been obstructed by the displacement indicator 182. When this occurs, the microcontroller 272 exits the loop and proceeds to program step 312.

Program step 312 is the point at which the microcontroller 272 calculates the amount of medium that has been dispensed as a result of the displacement of indicator 182 detected at step 308. This amount is substantially equal to the amount of medium that has been dispensed as a result of the indicator's 182 displacement to the first or second indicator positions (depending on the current valve position). As discussed above, this is a predetermined fixed volume equal to the amount of fluid dispensed from the first reservoir 188 when the displacement indicator 182 has reached the first indicator position (210 in FIG. 6A), or the amount of fluid dispensed from the second reservoir 190 when the indicator has reached the second indicator position (212 in FIG. 6B). Of course, the actual magnitude of the amount dispensed is dependent on the volume of the main fluid chamber 164, and on the actual locations selected for the first and second indicator positions. In the preferred embodiment, these variables are such that the amount dispensed is 0.4 milliliters. This fixed amount is added to the accumulator variable at program step 312.

In the preferred embodiment, in addition to this fixed amount, there is an additional amount of fluid dispensed that must be accounted for by the microcontroller 272 at program step 312. Because there is a finite time that elapses between the time that the indicator 182 is detected at step 310, and the time that the displacement device 100 is switched to the next valve position, an additional amount of fluid will be dispensed that must be accounted for. To do so, the microcontroller 272 calculates the velocity of the displacement indicator 182 based on the elapsed time value contained in the Displacement Indicator Travel Timer variable. The velocity of the displacement indicator 182 is essentially equal to the rate-of-fluid flow, which can be used to determine the amount of fluid that will be displaced during the time interval that it takes to switch the positive displacement device 100 to the next valve position. At program step 312, this additional "correction" amount is added to the accumulator variable, along with the predetermined fixed volume that is dispensed each time the fluid indicator 182 is displaced to a indicator position.

The microcontroller 272 will periodically generate an "electrical flow signal" and send it to the digital processor 220 (as is shown schematically at line 274 in FIG. 7). Preferably, this electronic flow signal is a single electrical pulse, which merely indicates that the sensor circuit 256 has detected that a fixed unit of fluid, one milliliter, has been dispensed. It will be appreciated that the fixed unit volume is largely arbitrary, and could be set to be most any manageable unit volume. Also, the electrical flow signal, instead of being in the form of a single pulse indicative of a fixed volume, could instead be comprised of a multiple line signal that serves to periodically relay directly to the digital processor 220 the exact amount of fluid that has been detected and calculated by the microcontroller 272.

Thus, having updated the accumulator value at program step 312, the microcontroller 272 proceeds to program step 313 where it checks the then current accumulator value. If the accumulator value is greater than a predetermined amount, such as one milliliter, the microcontroller 272 will proceed to program step 316, where that fixed value, one milliliter, is subtracted from the accumulator value. The microcontroller 272 then proceeds to program step 318, at which point it outputs the electrical flow signal "pulse" to the digital processor 220, which indicates that one milliliter of contrast medium has been dispensed.

If at program step 314, the microcontroller 272 instead determines that the accumulator value is still less than the predetermined amount, one milliliter, then it will refrain from yet outputting an electrical flow signal to the digital processor 220 until an additional amount of contrast medium has been dispensed and detected. In this situation, the microcontroller 272 proceeds directly to program step 320, where it saves the current accumulator value, and resets the Displacement Indicator Travel Timer to zero. The microcontroller 272 then proceeds to program step 322, where it outputs the appropriate control signal to the stepper motor driver circuit 276 so as to cause the stepper motor 278 to move the fluid cylinder 162 to the next valve position. Once in the new valve position, the microcontroller 272 returns to program step 308 where it begins monitoring the new emitter/detector optics pair corresponding to the new valve position. The above described steps are then repeated so as to provide a continuous monitoring and operation of the positive displacement device 100.

Figure 9A:
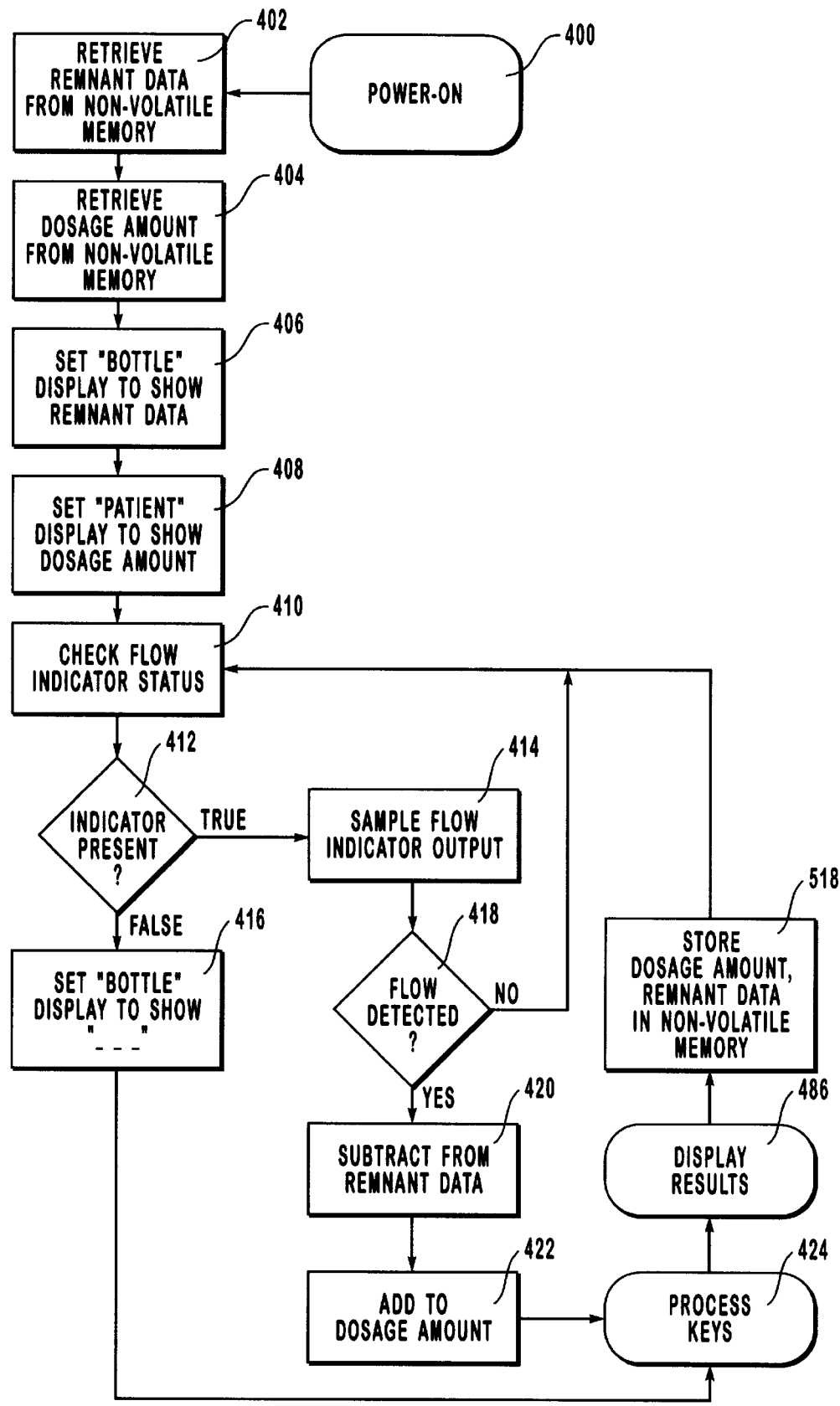
FIGS. 9A through 9C taken together illustrate a flow chart showing one presently preferred method for programming the digital processor of the electronic controller in FIG. 7.
Figure 9B:
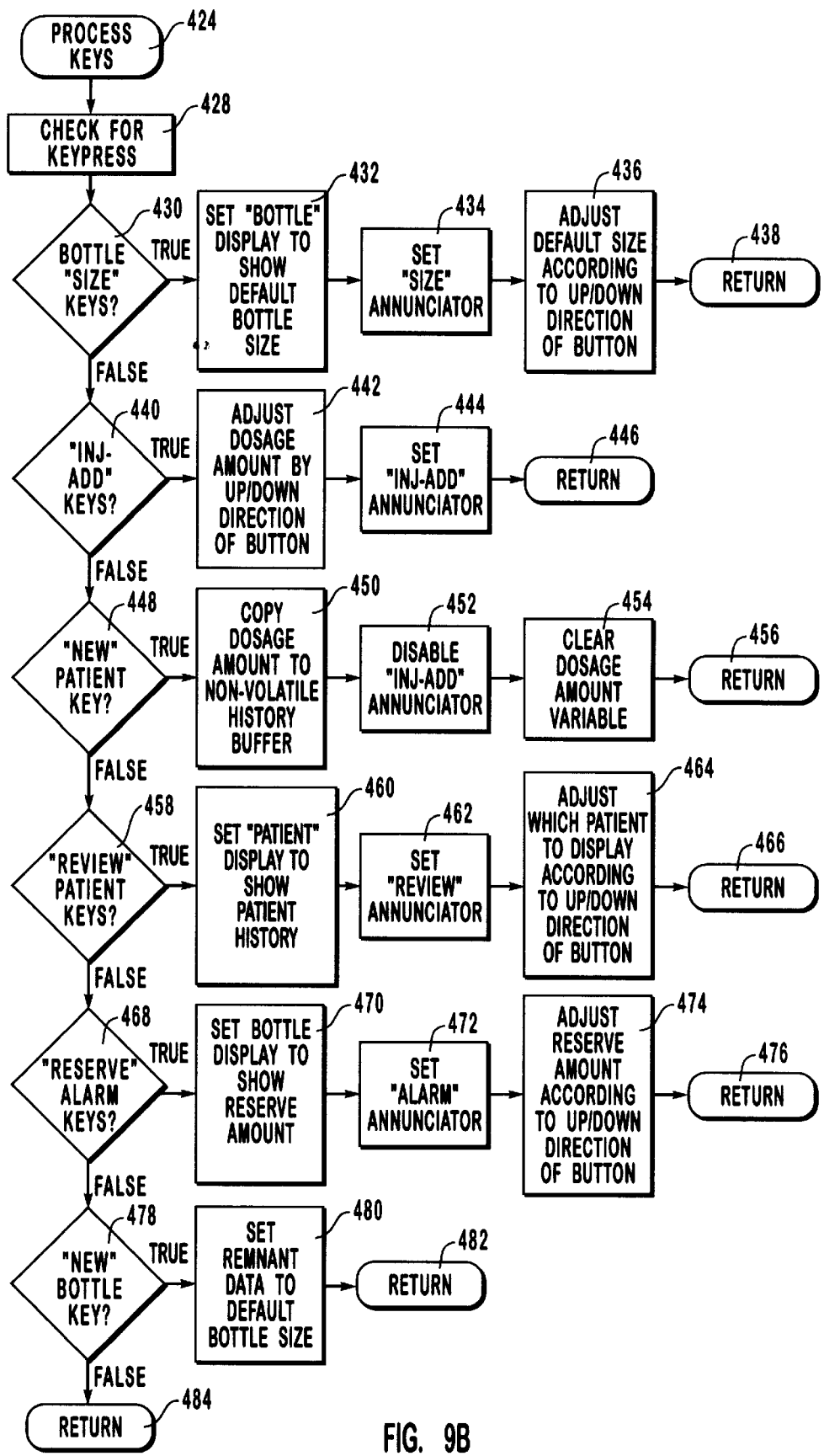
Figure 9C:
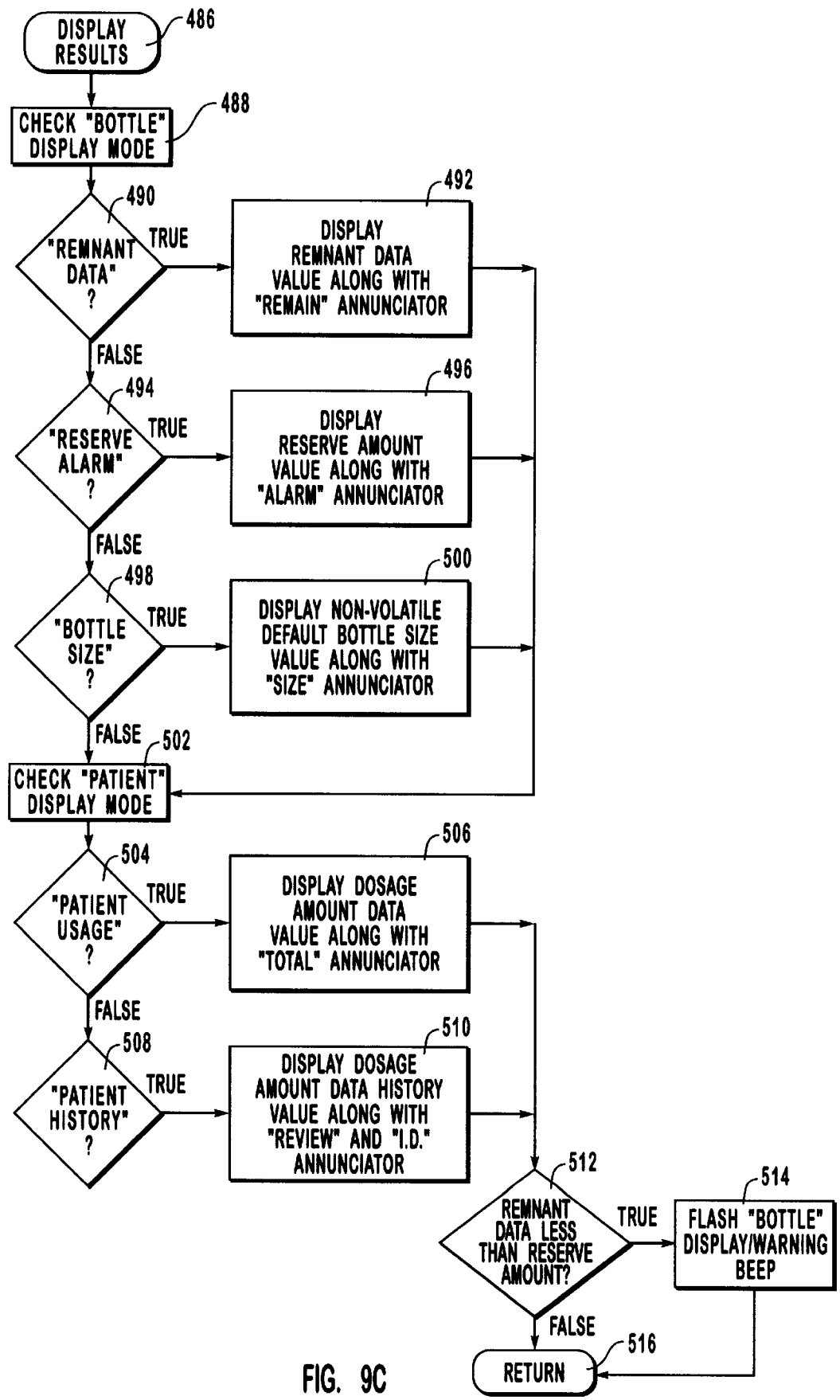

Reference will next be made to FIG. 9A, which illustrates the main portion of the preferred program instructions for controlling digital processor 220. When the electronic controller 106 is powered on, the program starts as indicated at program step 400 where the system initializes, and the appropriate program instructions are loaded from the program memory 228 into the digital processor 220. The digital processor 220 then moves to step 402, and retrieves a value from the nonvolatile memory 226 referred to as the "remnant data" variable, which indicates the amount of contrast media that remains in the current contrast media bottle or bag 10'. This step assumes that the amount of contrast medium left in a bag 10' will be tracked, even in the event of a loss of power by the electronic controller 106. After the remnant data variable is retrieved, the processor 220 next moves to program step 404 where it retrieves from the nonvolatile memory 226 a value contained in the "dosage amount" variable, which indicates, for the patient that is currently being treated, the cumulative amount of contrast medium that has been dispensed to this particular patient. Next, at program step 406 the processor 220 sets the display mode of the first digital readout 112 display portion of the controller 106 (the "Bottle" display) to display the value contained in the remnant data variable, previously retrieved from the nonvolatile memory 226 at step 402. The REMAIN annunciator 118 mode is also set to be illuminated at this step, indicating to the user that remnant data for the current media source is being displayed. Similarly, at program step 408 the processor 220 sets the display mode of the second digital readout 114 (the "Patient" display) so as to show the value contained in the dosage amount variable. Also, the TOTAL annunciator 124 mode is set to be illuminated, indicating to the user that dosage amount data for the current patient is being displayed.

The digital processor 220 next proceeds to program step 410, where it enters a program loop to monitor the status of the positive displacement device flow indicator 100 via the sensor circuit 256. In the presently preferred method, program steps 410 and 412 are optional, and are dependent on the configuration and setup of the electronic controller 106. The "status" checked at program step 410 could be, for instance, information that is specific to the particular flow indicator, such as an indicator type, calibration information, etc. Additionally, the status information obtained could merely be whether a positive displacement device 100 is operatively connected to the electronic controller 106. This could be accomplished, for instance, by adding an additional optical emitter, detector pair, which are positioned so as to detect whether a displacement device 100 is present and/or properly connected. Thus, if what is being checked at program step 408 is whether a displacement device 100 is connected, then at program step 412 the processor 220 performs a decisional step that is based on the results of that query. If at program step 410 the processor 220 detects that the displacement device 100 is not connected, then step 412 will cause the processor 220 to proceed directly to program step 416. At step 416, the processor 220 alerts the user that a displacement device 100 is not yet operatively connected to the electronic controller 106. In the preferred embodiment, this is done by setting the display mode of the second digital readout 114 portion of the controller 106 display to alert the user that the flow indicator is not properly connected. In the preferred embodiment, this is done by displaying blanks on the digital readout 114.

If at steps 410 and 412 the processor 220 instead determines that the device 100 is present and operatively connected to the electronic controller 106, it proceeds to program step 414. At step 414 the digital processor 220 monitors the electrical flow signal that is generated by the sensor circuit 256 and schematically shown at line 274 in FIG. 7. If no flow is detected at program step 418, indicated by the absence of any electrical flow signal, the processor 220 will loop back to program step 410 and will continue processing program steps 412, 414 and 418 until such time that flow is detected, i.e., as indicated by the presence of an electrical flow signal pulse.

When fluid flow is detected by the digital processor 220 at steps 414 and 418, the processor 220 then proceeds to program step 420. Program step 420 is the point at which the processor 220 tracks the cumulative amount of contrast medium remaining within the contrast media bag 10', the remnant data value. To do so, the digital processor 220 subtracts the amount detected at step 414 as a result of receiving the electrical flow signal pulse (1 milliliter in the preferred embodiment) from the current value contained in the remnant data variable. The new value contained in the remnant data variable represents the current amount of contrast medium that remains in the bag 10'. Preferably, the display mode of the "bottle" digital readout 112 is set so as to continuously display the contents of this variable. The REMAIN annunciator 118 mode is also set to remain illuminated. In this way, the user of the system is continuously updated as to the amount of medium that remains in the source 10'.

In addition to continuously updating the amount of contrast medium that remains within the bag 10', the processor 220 also tracks the cumulative amount of contrast medium that has been delivered to the current patient, i.e., the dosage amount data. This is done at program step 422, where the digital processor 220 adds the amount detected at step 414 to the current contents of the dosage amount variable. The new value indicates the total amount of contrast medium that has been administered to the current patient. Preferably, the display mode of the "patient" digital readout 114 is set to display the contents of this variable. The TOTAL annunciator 124 mode is also set to remain illuminated.

After performing step 422 (or step 416 if the displacement device 100 isn't operatively connected as determined at steps 410, 412 and 416) the digital processor 220 proceeds to program step 424. This program step causes the digital processor 220 to perform a set of program steps collectively referred to as "Process Keys," which are shown in greater detail in FIG. 9B, to which reference is now made.

As previously described in conjunction with FIG. 3, the control panel 110 of the electronic controller 106 is equipped with a series of touch-sensitive button switches or keys that can be actuated by the user to control which one of a number of different functions are performed by the digital processor 220. To summarize, in the presently preferred embodiment, the button switches available are: "SIZE" switch 130, "NEW" switch 132, an "ALARM" switch 134, a "REVIEW" switch 136, a "NEW" switch 138, and an "INJ-ADD" switch 140. The functions provided by each of these switches are controlled by the process steps illustrated in FIG. 9B.

After entering the Process Keys routine at program step 424, the digital processor 220 proceeds to program step 428 where it determines which of the above switches have been depressed by a user. Beginning at step 430, the processor 220 queries whether the "SIZE" switch 130 was actuated. In the preferred embodiment, the electronic controller 106 maintains in non-volatile data memory 226 a "default bottle size" value, which is preset to two-hundred (200) milliliters. When a new bottle or bag 10' is connected, the amount of contrast medium contained within it will be presumed to be equal to this default size. However, this default size can be modified by the user by manipulating the "SIZE" switch 30. Thus, if at program step 430, the digital processor 220 determines that the "SIZE" switch 130 has been depressed by the user, the processor 220 proceeds to program step 432, where it retrieves the "default bottle size" value from nonvolatile data memory 226 and sets the display mode of the first digital readout 112 to display this default value (thereby disabling the display of the current remnant data value). The processor next proceeds to program step 434 where it sets the "SIZE" annunciator 116 mode of the electronic controller 106 display to be illuminated, thereby indicating to the user that, if needed, the "default bottle size" value currently being displayed can be modified, if for example, a different size bag 10 is to be used (at the same time, the REMN annunciator 118 mode is disabled). At program step 436 the processor 220 monitors the dual-direction "SIZE" switch 130, which is separated into "up" and "down" portions. If the "SIZE" switch 130 is pressed in the "up" direction, the "default bottle size" will be incremented by 25 milliliters (or other suitable default value). In the preferred embodiment, if the "default bottle size" reaches a maximum value of 300 milliliters, it will remain at this value and not increment any further. Conversely, if the "SIZE" button is pressed in the "down" direction, the "default bottle size" will by decremented by 25 milliliters. In the preferred embodiment, if the bottle size reaches a minimum value of 50 milliliters, it will remain at this value and cannot be decremented any further.

Each time the "SIZE" switch 130 is pressed, an internal timer is set. After this timer accumulates a predetermined elapsed time, three (3) seconds in the preferred embodiment, the mode of the first digital readout 112 portion of the electronic controller display will be set to revert back to display the then current remnant data value. Also, when the timer accumulates three (3) seconds, the "SIZE" annunciator 116 mode is disabled, and the "REMAIN" annunciator 118 set to be illuminated.

Once the "default bottle size" variable has thus been adjusted, the digital processor 220 proceeds to program step 438 and returns to the main portion of the program method illustrated in FIG. 9A.

If at program step 430 the digital processor 220 determines that the "SIZE" switch 130 has not been pressed, the processor 220 instead proceeds to program step 440. At this step, the digital processor 220 queries whether "INJ-ADD" button switch 140 has been pressed by the user. If so, the digital processor 220 proceeds directly to program step 442, and begins performing a series of functional steps corresponding to the "INJ-ADD" switch 140. As previously noted, the amount of contrast that has been administered to the current patient is automatically computed on a continuous basis, and is displayed in real time on the "patient" digital display 114. As contrast media flow is detected and accumulated, that amount is added to the amount, contained in the dosage amount variable, that has already been dispensed to the current patient. However, in the preferred embodiment, the user also has the option of adjusting the dosage amount for the current patient by operating the dual-direction "INJ-ADD" button switch 140. At program step 436, the dosage amount value for the patient will be increased or decreased, depending on whether the positive or negative direction portions of switch 140 are pressed, by two (2) milliliters (or any other suitable amount) upon each actuation of the switch 140. The first actuation of the "INJ-ADD" switch 140 causes the "INJ-ADD" annunciator 126 mode to set to illuminate at program step 444, which remains illuminated until the "NEW" button switch 138 is depressed. Once the dosage amount value has been adjusted to the user's satisfaction, the digital processor 220 proceeds to program step 446, at which point the program returns to the main program steps illustrated on FIG. 9A.

Thus, the "INJ-ADD" button switch 140 provides the user with the ability to manually override the automatic monitoring of the contrast flow, and to adjust the amount contained in the dosage amount variable as needed. This may be necessary, for instance, if the patient has already been administered an amount of contrast medium not monitored by the electronic controller 106.

If at program step 440 the digital processor 220 does not detect the actuation of "INJ-ADD" switch 140, it instead proceeds to program step 448, where it checks the status line corresponding to the "NEW" patient key 138. As the name implies, a user will actuate the "NEW" patient key 138 when the user has completed the administration of contrast medium to the current patient, and wishes to re-set the system to begin monitoring a new patient.

Thus, if at program step 448, the digital processor 220 detects actuation of the "NEW" patient key 138, it proceeds to program step 450. At this step, the digital processor 220 first saves the contents of the dosage amount variable for the current patient into a patient history buffer within nonvolatile data memory 226. In this way, the amount of contrast medium administered to this patient is retained for later retrieval and review by the user. Preferably, a history of the last four to seven patients will be stored in the history buffer location of nonvolatile memory 226 and each patient will be assigned a "patient I.D." number, assigned by counting backward from the "current" patient being dosed. (i.e., the patient dosed immediately prior to the current patient shall be termed as "Patient 1"). Each time the "NEW" patient button key 138 is pressed, the current patient's dosage amount will be stored and the values for prior patients will be preserved (and their associated patient I.D. numbers will be incremented by one). The "oldest" patient data will be purged from the buffer. Preferably, this update of the patient history buffer will not take place in the event that the current patient's dosage amount is zero.

Having updated the patient history buffer at program step 450, the digital processor 220 then proceeds to program step 452, where it disables the "INJ-ADD" annunciator 126 mode if it was previously set to be illuminated. Next, the digital processor 220 proceeds to program step 454, where it clears the contents of the current dosage amount variable for the new patient. The system now has been reinitialized and can begin monitoring flow data for the new patient. The digital processor 220 then proceeds to program step 456, and returns to the main program illustrated in FIG. 9A.

If at program step 448, the digital processor 220 does not detect the actuation of the "NEW" patient key 138, it instead proceeds to program step 458. At program step 458, the digital processor 220 checks the status of the "REVIEW" patient switch 136. This key 136 allows the user to review the accumulated dosage amounts for the previous patients that have been stored in the patient history buffer in nonvolatile data memory 226. Thus, at program step 460, the digital processor 220 will set the patient digital display 114 to display the historical dosage amount value for the selected patient. The patient I.D. of the particular historical patient that is to be displayed will be reflected by illuminating the appropriate patient I.D. annunciator 128, at program step 462. At program step 464 the processor 220 determines which historical patient to display. If the dual direction patient "REVIEW" switch 136 is pressed in the "up" direction, the patient I.D. annunciator 128 will be set to advance to the next number (or to the number "1" annunciator if the patient display 114 previously displayed the dosage amount for the current patient). The dosage amount value for that particular historical patient will then be retrieved from the patient history buffer portion of nonvolatile data memory 226, and will be set to be displayed on the patient digital dislay 114.

In the same manner, if the patient "REVIEW" switch 136 is pressed in the "down" direction, the patient I.D. annunciator 128 will be set to advance backward to the previous patient I.D. number (or to the highest patient I.D. number, if the patient display 114 previously held the contents of the current patient). In the event that the patient I.D. number annunciator 128 is decremented below "1" the digital processor 220 shall "wrap" back to the highest patient I.D. number ("5" in the preferred embodiment).

In the preferred embodiment, each time the patient "REVIEW" switch 136 is pressed, an arbitrary timer is reset. After this timer accumulates three (3) seconds (or any other suitable elapsed time), the patient display 114 will revert back to the display of the current patient's dosage amount value. At the same time, the "REVIEW" 122 and patient I.D. 128 annunciators will be disabled.

Having set the appropriate display modes to display patient history information, the digital processor 220 then proceeds to program step 466, which causes the processor 220 to return to the main portion of the program method illustrated in FIG. 9A.

If at program step 458 the digital processor 220 does not detect the actuation of the patient "REVIEW" key 136, it proceeds directly to program step 468 where it checks the appropriate status line to determine whether the reserve "ALARM" key 134 has been actuated. As was previously noted in Part I above, the preferred embodiment of the electronic controller 106 includes an alarm means, which functions to alert the system user when the amount of contrast medium that remains within the contrast medium source 10' (remnant data) falls below a certain predefined "reserve alarm" level. The default value for this reserve alarm level, which is stored in a data location within the nonvolitile data memory 226, is twenty (20) milliliters. However, this default value can be modified by the user by way of the reserve "ALARM" key 134.

Thus, if the digital processor 220 detects that this key 134 has been actuated at program step 468, it proceeds to program step 470 and sets the display mode for the bottle digital display 112 to show the current value contained in the reserve alarm variable. The digital processor 220 at program step 472 sets the "ALARM" annunciator 120 to be illuminated, and then proceeds to program step 474. At that step, the digital processor 220 adjusts the value contained in the reserve alarm variable in response to the user's manipulation of the dual-direction reserve "ALARM" key 134. Each time the "ALARM" key 134 is pressed in the up direction, the value contained in the reserve alarm variable is incremented by five (5) milliliters (or any other suitable amount). In the preferred embodiment, if the reserve alarm value reaches a maximum value of forty (40) milliliters, it will remains at this value and not advance. If the "ALARM" key 134 is pressed in the down direction, the value contained in the reserve alarm variable will be decremented by five (5) milliliters. In the preferred embodiment, if the reserve alarm value reaches a minimum value of zero (0) milliliters, it will remain at this value and will not decrement to a negative value.

Preferably, each time that the reserve "ALARM" key 134 is pressed, an arbitrary timer is reset, and begins tracking elapsed time. After this timer accumulates three (3) seconds (or any other suitable elapsed time), the bottle digital display readout 112 will revert back and be set to display the amount of contrast medium that is left in the current bottle, i.e., the remnant data value. At the same time, the "REMAIN" annunciator 118 will be set to be illuminated, and the "ALARM" annunciator 120 will be disabled. Thus, by manipulating the reserve "ALARM" key 134, the user can define the point at which he or she will be alerted when the source 10' is almost empty, by way of the alarm means discussed above. In addition to sounding an audible alarm (shown in FIG. 7 at functional box 252), the digital processor 220 may optionally be programmed to flash the contents of the bottle digital display 112 until such time that the user activates the "NEW" bottle switch 132.

If at program step 468, the digital processor 220 does not detect the actuation of the reserve "ALARM" key 134, the processor 220 instead proceeds to program step 478, where it checks the status of the "NEW" bottle switch 132. This switch 132 allows the user to reset the necessary variables when a new bottle/bag 10' is attached to the system. Thus, at program step 480, the digital processor 220 will reset the value contained in the remnant data variable to be equal to the default bottle size that is stored in a nonvolitile data memory location 226. This default size, as noted above, is set to two hundred (200) milliliters, which can then be varied by the user by way of the dual-direction bottle "SIZE" key 130 discussed above. This new remnant data value will then be set to be displayed on the bottle digital display 112, along with the illumination of the "REMAIN" annunciator 118.

If the digital processor 220 does not detect the actuation of the "NEW" bottle switch 132 at program step 478, the processor 220 instead proceeds to program step 484, whereupon it returns to the body of the main program illustrated in FIG. 9A, to which reference is again made.

Having performed the functional program steps corresponding to the "Process Keys" program step at 424, the digital processor 220 next proceeds to the "Display Results" portion of the program shown at program step 486. This portion of the program steps functions so as to have the processor 220 cause the appropriate digital displays 112, 114 and associated annunciators to output the appropriate digital flow data. One preferred example of the program steps used to implement this function are illustrated in more detail in FIG. 9C, to which reference is now made.

Having entered this portion of the program at program step 486, the digital processor 220 first proceeds to program step 488, where it evaluates the current display mode for the "Bottle" digital display 112 and its associated annunciators 116, 118 and 120. Depending on the status of the current display mode, the digital processor 220 will cause the necessary data to be electronically displayed.

Beginning with program step 490, the digital processor 220 determines whether the current display mode should include a display of remnant data. If the bottle display mode is set to display remnant data, then the digital processor 220 at program step 492 will cause the contents of the remnant data variable to be displayed on the bottle digital display 112, and will also cause the "REMAIN" annunciator 118 to be illuminated. The digital processor 220 will then proceed directly to program step 502.

If the bottle display mode is not set to display the remnant data value, then the digital processor 220 will proceed directly from program step 490 to program step 494, where it determines whether the display mode is such that the minimum reserve amount value should be displayed. If so, the digital processor 220 proceeds to program step 496, where it causes the contents of the reserve amount variable to be displayed on the bottle digital display 112 and at the same time causes the "ALARM" annunciator 120 to be illuminated. The digital processor 220 then proceeds directly to program step 502.

If the display mode is not set to display either remnant data or minimum reserve amount data, then the digital processor 220 proceeds to program step 498, where it determines if the display mode is set to display the contents of the default bottle size variable. If so, the digital processor 220 proceeds to program step 500 where it causes the current contents of the bottle default size variable to be displayed in the bottle digital display 112, and also causes the "SIZE" annunciator 116 to be illuminated. The digital processor 220 then proceeds directly to program step 502.

At program step 502, the digital processor 220 checks the status of the "Patient" display 114, and its associated annunciators 122, 124, 126 and 128. The digital processor 220 then proceeds to program step 504, where it determines if the display mode requires a display of the dosage amount data for the current patient. If so, the digital processor 220 causes the current contents of the dosage amount variable to be displayed on the patient digital display 114, while at the same time causing the "TOTAL" annunciator 124 to be illuminated. The digital processor 220 then proceeds to program step 512.

If at program step 504 the status of the patient display mode does not require the display of current patient dosage amount data, the processor 220 instead proceeds to program step 508, where it determines if the patient history information should be displayed instead. If so, the digital processor 220 causes the dosage amount data for a past patient to be displayed on the patient digital display 114. It also causes the "REVIEW" annunciator 122 to be illuminated along with the corresponding patient I.D. annunciator 128.

After performing either of the program steps at 506 or 510, the digital processor 220 proceeds to program step 512 where it determines if the current remnant data value is less than the current reserve alarm amount. If it is, then the digital processor 220, at step 514, will actuate the alarm means so as to cause an audible warning to sound, and if desired, will also cause the contents of the bottle digital display 114 to flash.

If at program step 512 it is instead determined that the contents of the remnant data variable are greater than the prescribed reserve alarm amount, then the digital processor 220 proceeds directly to program step 516, whereupon it returns to the main program in FIG. 9A, to which reference is again made.

After having processed the keys in program step 424, and displaying the appropriate results on the digital displays 112, 114, the digital processor 220 then proceeds to program step 518, where it stores in the nonvolatile memory location 226 the then current dosage amount value and the remnant data value. In this way, these values are stored by the system on a real-time basis so as to preserve the respective values at a subsequent power-on, or restoration of power after an unscheduled power loss. The processor 220 then returns to program step 410, and continues to process program steps in the manner described above.

In summary, the set of program steps illustrated in FIG. 8, and FIGS. 9A through 9C, constitute one presently preferred example of the program method used to cause the electronic controller 106 to continuously monitor the flow of contrast medium to a patient. Advantageously, the method provides the user with digital flow data in real time, insuring that the administration of the contrast medium is done safely and efficiently.

It will be appreciated that the digital processor 220 can be programmed so as to implement the above-described method using any one of a variety of different programming techniques and programming languages.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for monitoring the amount of parenteral fluid that is dispensed from a parenteral fluid source to a patient through a fluid conduit, the system comprising:

fluid flow indicator means for indicating the amount of parenteral fluid that is dispensed through the fluid conduit to the patient, the fluid flow indicator means being placed in fluid communication with the parenteral fluid; and an electronic controller comprising:

sensor means for operatively interfacing the electronic controller with the fluid flow indicator means so as to detect the indicated amount of parenteral fluid that is dispensed through the fluid conduit, and for generating an electrical flow signal that is representative of said indicated amount;

digital processor means for receiving the electrical flow signal and for electronically processing the electrical flow signal so as to derive therefrom digital flow data representing (a) remnant data that represents the magnitude of the total amount of parenteral fluid still remaining within the parenteral fluid source, and (b) dosage amount data that represents the magnitude of the total amount of parenteral fluid delivered to the patient; and display means, electronically connected to the digital processor means, for selectively outputting a visually perceivable display of the digital flow data simultaneously showing a real-time status of both the amount of parenteral fluid remaining at the source as well as a status of the total amount of parenteral fluid delivered to the patient.

2. A system as defined in claim 1, wherein the electronic controller further comprises means for coupling the electronic controller to the fluid flow indicator means in a detachable manner, and the amount of parenteral fluid that is dispensed through the fluid conduit to the patient indicated by the flow indicator means being thereafter detected by the sensor means, such that the fluid flow indicator means is detachable from the electronic controller upon completion of monitoring, and the electronic controller then re-used.

3. A system as defined in claim 1, wherein the electronic controller further includes data memory means for storing the digital flow data for later retrieval and output.

4. A system as defined in claim 1, wherein the electronic controller further includes program memory means for storing machine-readable instructions utilized by said digital processor means to electronically process the electrical flow signal so as to derive therefrom the digital flow data.

5. A system as defined in claim 1, wherein the electronic controller further includes a control panel, and wherein the display means comprises a first and a second digital readout formed on the control panel.

6. A system as defined in claim 1, wherein the electronic controller further includes: switch means, located on a control panel formed on the electronic controller, for selecting at least one of the following optionally selectable functions to be performed by the digital processor means:

(a) displaying on the display means a remnant data value, the remnant data value being the magnitude of the total amount of parenteral fluid still remaining within the parenteral fluid source; and (b) displaying on the display means a dosage amount data value, the dosage amount data value being the magnitude of the total amount of parenteral fluid delivered to the patient.

7. A system as defined in claim 6, wherein the optionally selectable functions further include:

(a) setting a default size value for the parenteral fluid source;

(b) setting a minimum reserve amount alarm value;

(c) retrieving and then displaying on the display means a historical patient data value, the historical patient data value being the magnitude of the total amount of parenteral fluid delivered to a prior patient; and (d) modifying the dosage amount data value.

8. A system as defined in claim 1 further comprising alarm means for electrically outputting an alarm indicator to a system user that signals when an amount of parenteral fluid that remains within the parenteral fluid source falls below a predetermined level.

9. A system as defined in claim 1, wherein the parenteral fluid is a contrast medium.

10. A system as defined in claim 1, wherein the fluid flow indicator means comprises a positive displacement device comprising:

inlet chamber means for receiving the parenteral fluid from the fluid conduit;

outlet chamber means for returning the parenteral fluid received at the inlet chamber means to the fluid conduit;

means for defining a main fluid chamber;

at least one fluid communication path between the inlet chamber means, the main fluid chamber and the outlet chamber means; and displacement indicator means, movably disposed within the main fluid chamber in response to a fluid pressure, for indicating the displacement of a predetermined measured volume of parenteral fluid through the outlet chamber means via the at least one fluid communication path based on the position of the indicator means within the main fluid chamber.

11. A system as defined in claim 10, wherein the positive displacement device further comprises valve means for selectively defining a first fluid communication path and a separate second fluid communication path, the first and the second fluid communication paths each providing a path of fluid communication between the inlet chamber means, the main fluid chamber, and the outlet chamber means.

12. A system as defined in claim 11, wherein the valve means is selectively operable between the first fluid communication path and the second fluid communication path by moving the main fluid chamber relative to both the inlet chamber means and the outlet chamber means.

13. A system as defined in claim 11, wherein the sensor means includes:

means for providing a displacement signal when the displacement indicator means is displaced to at least one predetermined indicator position within the main fluid chamber, thereby indicating the displacement of a predetermined measured volume of parenteral fluid through the displacement device;

means for operating the valve means alternately between the first fluid communication path and the second fluid communication path; and controller means for monitoring the displacement signal and generating in response thereto the electrical flow signal that is representative of the indicated amount of parenteral fluid dispensed through the positive displacement device.

14. A system as defined in claim 13, wherein the means for providing a displacement signal comprises an optical sensing circuit positioned within the electronic controller so as to be capable of optically detecting when the displacement indicator means has been displaced within the main fluid chamber to the at least one predetermined indicator position and then generating the displacement signal.

15. A system as defined in claim 13, wherein the means for operating the valve means comprises a motor circuit having a digitally controllable motor operatively connected to the positive displacement device and that physically manipulates the valve means between first fluid communication path and the second fluid communication path in response to a predetermined control signal.

16. A system as defined in claim 13, wherein the controller means comprises a programmable digital processor that is operatively coupled to the means for providing a displacement signal and the means for operating the valve means.

17. A system as defined in claim 10, wherein the displacement indicator means comprises a fluid displacement indicator having a first end and an opposite second end, the indicator being sized so as to be movably disposed within the main fluid chamber when a fluid pressure is applied to either of the first or the second ends, the displacement indicator being disposed within the main fluid chamber so as to define a fluid-tight first variable sized reservoir formed by the first end and the main fluid chamber, and a fluid-tight second variable sized reservoir formed by the opposite second end and the main fluid chamber.

18. A system for monitoring the amount of parenteral fluid that is dispensed from a parenteral fluid source to a patient through a fluid conduit, the system comprising:

fluid flow indicator means for indicating the amount of parenteral fluid that is dispensed through the fluid conduit to the patient, the fluid flow indicator means being placed in fluid communication with the parenteral fluid; and an electronic controller comprising:

digital processor means, responsive to the amount of parenteral fluid dispensed through the fluid conduit to the patient indicated by the fluid flow indicator means, for electronically processing the amount so as to electronically monitor and display the amount of parenteral fluid delivered from the parenteral fluid source and the amount delivered to the patient by performing the steps of:

(a) deriving remnant data that represents a numerical value of the magnitude of the total amount of parenteral fluid still remaining within the parenteral fluid source;

(b) deriving dosage amount data that represents a numerical value of the magnitude of the total amount of parenteral fluid delivered to the patient;

(c) electronically storing at least one of said derived data values for later retrieval and output; and (d) selectively displaying said derived data values in a visually perceptible manner to a system user; and display means, electronically connected to the digital processor means, for outputting a visually perceivable display of the derived data values simultaneously showing a real-time status of both the amount of parenteral fluid remaining at the source as well as a status of the total amount of parenteral fluid delivered to the patient.

19. A system as defined in claim 18 wherein the electronic controller further comprises:

means for coupling the electronic controller to the fluid flow indicator means in a detachable manner; and sensor means for operatively interfacing the electronic controller with the fluid flow indicator means so as to detect the indicated amount of parenteral fluid that is dispensed through the fluid conduit to the patient when the fluid flow indicator means is detachably coupled to the electronic controller, and for generating therefrom for use by the digital processor means an electrical flow signal that is representative of said indicated amount, and whereby the fluid flow indicator means is detachable from the electronic controller upon completion of monitoring, and the electronic controller then re-used.

20. A system as defined in claim 19, wherein the electronic controller further includes data memory means for storing at least one of said derived data values for later retrieval and output.

21. A system as defined in claim 20, wherein the electronic controller further includes program memory means for storing machine-readable instructions utilized by said digital processor means to electronically carry out said program steps.

22. A system as defined in claim 21, wherein the electronic controller further includes a control panel, and wherein the display means comprises a first and a second digital readout formed on the control panel.

23. A system as defined in claim 22, wherein the electronic controller further includes:

switch means, located on the control panel, for selecting at least one of the following optionally selectable functions to be performed by the digital processor means:

(a) displaying on the first digital readout the remnant data value;

(b) displaying on the second digital readout the dosage amount data value;

(c) setting a default size value for the parenteral fluid source;

(d) setting a minimum reserve amount alarm value;

(e) retrieving and then displaying on the second digital readout a historical patient data value, the historical patient data value being the magnitude of the total amount of parenteral fluid delivered to a prior patient; and (f) modifying the dosage amount data value.

24. A system as defined in claim 23 further comprising alarm means for electrically outputting an alarm indicator to a system user that signals when an amount of parenteral fluid that remains within the parenteral fluid source falls below the minimum reserve amount alarm value.

25. A system as defined in claim 24, wherein the parenteral fluid is a contrast medium.

26. A system as defined in claim 18, wherein the fluid flow indicator means comprises a positive displacement device comprising:

inlet chamber means for receiving the parenteral fluid from the fluid conduit;

outlet chamber means for returning the parenteral fluid received at the inlet chamber means to the fluid conduit;

means for defining a main fluid chamber;

valve means for selectively defining either a first fluid communication path or a separate second fluid communication path, the first and the second fluid communication paths each providing a fluid communication path between the inlet chamber means, the main fluid chamber, and the outlet chamber means; and displacement indicator means, movably disposed within the main fluid chamber in response to a fluid pressure, for indicating the delivery of a predetermined measured volume of parenteral fluid through the outlet chamber means via the first fluid communication path, corresponding to the indicator means being in a first indicator position, or via the second fluid communication path, corresponding to the indicator means being in a second indicator position.

27. A system as defined in claim 26, wherein the sensor means includes:

means for providing a displacement signal when the displacement indicator means is in the first indicator position or in the second indicator position;

means for operating the valve means alternately between the first fluid communication path and the second fluid communication path; and controller means for monitoring the displacement signal and generating in response thereto the electrical flow signal that is representative of the indicated amount of parenteral fluid dispensed through the positive displacement device.

28. A system as defined in claim 27, wherein the means for providing a displacement signal comprises an optical sensing circuit positioned within the electronic controller so as to be capable of optically detecting when the displacement indicator means has been displaced within the main fluid chamber to the first indicator position and to the second indicator position and then generating the displacement signal.

29. A system as defined in claim 28, wherein the means for operating the valve means comprises a motor circuit having a digitally controllable motor operatively connected to the positive displacement device and that physically manipulates the valve means between first fluid communication path and the second fluid communication path in response to a predetermined control signal.

30. A system as defined in claim 29, wherein the controller means comprises a programmable digital processor that is operatively coupled to the means for providing a displacement signal and the means for operating the valve means.

31. A system as defined in claim 30, wherein the valve means is selectively operable between the first fluid communication path and the second fluid communication path by physically moving the main fluid chamber relative to both the inlet chamber means and the outlet chamber means.

32. A system as defined in claim 31, wherein the displacement indicator means comprises a fluid displacement indicator having a first end and an opposite second end, the indicator being sized so as to be movably disposed within the main fluid chamber when a fluid pressure is applied to either of the first or the second ends, the displacement indicator being disposed within the main fluid chamber so as to define a fluid-tight first variable sized reservoir formed by the first end and the main fluid chamber, and a fluid-tight second variable sized reservoir formed by the opposite second end and the main fluid chamber.

33. A system as defined in claim 32, wherein the valve means comprises:

a first valve position which defines the first fluid communication path, and wherein the first fluid communication path includes a first input path between the inlet chamber and the first reservoir, and a first output path between the outlet chamber and the second reservoir; and a second valve position which defines the second fluid communication path, and wherein the second fluid communication path includes a second input path between the inlet chamber and the second reservoir, and a second output path between the outlet chamber and the first reservoir.

34. A system for monitoring the amount of parenteral fluid that is dispensed from a parenteral fluid source to a patient through a fluid conduit, the system comprising:

fluid flow indicator means for indicating the amount of parenteral fluid that is dispensed through the fluid conduit to the patient, the fluid flow indicator means being placed in fluid communication with the parenteral fluid; and an electronic controller comprising:
  means for coupling the electronic controller to the fluid flow indicator means in a detachable manner;
  sensor means for operatively interfacing the electronic controller with the fluid flow indicator means so as to optically detect the indicated amount of parenteral fluid that is dispensed through the fluid conduit to the patient when the fluid flow indicator means is detachably coupled to the electronic controller, and for generating therefrom an electrical flow signal that is representative of said indicated amount, and whereby the fluid flow indicator means is detachable from the electronic controller upon completion of monitoring, and the electronic controller then re-used;
  digital processor means for electronically processing the electrical flow signal so as to electronically monitor and display the amount of parenteral fluid dispensed from the parenteral fluid source to the patient by performing the steps of:
    (a) deriving remnant data that represents a numerical value of the magnitude of the total amount of parenteral fluid still remaining within the parenteral fluid source;
    (b) deriving dosage amount data that represents a numerical value of the magnitude of the total amount of parenteral fluid delivered to the patient;
    (c) electronically storing said derived data values for later retrieval and output; and
    (d) selectively displaying said derived data values in a visually perceptible manner to a system user;
  data memory means for storing at least one of said derived data values for later retrieval and output;
  program memory means for storing machine-readable instructions utilized by said digital processor means to electronically carry out said program steps; and
  display means, electronically connected to the digital processor means, for outputting a visually perceivable display of the derived data values simultaneously showing a real-time status of both the amount of parenteral fluid remaining at the source as well as a status of the total amount of parenteral fluid delivered to the patient.

35. A system as defined in claim 34, wherein the electronic controller further includes:

a control panel and wherein said display means comprises a digital readout on the control panel; and switch means, located on the control panel, for selecting at least one of the following optionally selectable functions to be performed by the digital processor means:

(a) displaying on the digital readout the remnant data value;

(b) displaying on the digital readout the dosage amount data value;

(c) setting a default size value for the parenteral fluid source;

(d) setting a minimum reserve amount alarm value;

(e) retrieving and then displaying on the digital readout a historical patient data value, the historical patient data value being the magnitude of the total amount of parenteral fluid delivered to a prior patient; and (f) modifying the dosage amount data value.

36. A system as defined in claim 34, wherein the parenteral fluid is a contrast medium.

37. A system as defined in claim 34, wherein the fluid flow indicator means comprises a positive displacement device comprising:

inlet chamber means for receiving the parenteral fluid from the fluid conduit;

outlet chamber means for returning the parenteral fluid received at the inlet chamber means to the fluid conduit;

means for defining a main fluid chamber;

fluid displacement indicator having a first end and an opposite second end, the indicator being sized so as to be movably disposed within the main fluid chamber between a first and a second indicator position when a fluid pressure is applied to either of the first or the second ends, the displacement indicator being disposed within the main fluid chamber so as to define a fluid-tight first variable sized reservoir formed by the first end and the main fluid chamber, and a fluid-tight second variable sized reservoir formed by the opposite second end and the main fluid chamber;

a first valve position which defines a first fluid communication path, the first fluid communication path including a first input path between the inlet chamber means and the first reservoir, and a first output path between the outlet chamber means and the second reservoir; and a second valve position which defines a second fluid communication path, the second fluid communication path including a second input path between the inlet chamber means and the second reservoir, and a second output path between the outlet chamber means and the first reservoir.

38. A system as defined in claim 37, wherein the sensor means includes:

means for optically monitoring the position of the fluid displacement indicator within the main fluid chamber and for providing a displacement signal when the fluid displacement indicator is in the first indicator position or in the second indicator position;

means for alternatively switching the positive displacement device between the first valve position and the second valve position; and controller means for monitoring the displacement signal and for generating in response thereto the electrical flow signal that is representative of the indicated amount of parenteral fluid dispensed through the positive displacement device.

39. A system as defined in claim 38, wherein the means for providing a displacement signal comprises an optical sensing circuit positioned within the electronic controller so as to be capable of optically detecting when the displacement indicator means has been displaced within the main fluid chamber to the first indicator position and to the second indicator position and then generating the displacement signal.

40. A system as defined in claim 39, wherein the means for operating the valve means comprises a motor circuit having a digitally controllable moter operatively connected to the positive displacement device and that physically manipulates the valve means between first fluid communication path and the second fluid communication path in response to a predetermined control signal.

41. A system as defined in claim 40, wherein the controller means comprises a programmable digital processor that is operatively coupled to the means for providing a displacement signal and the means for operating the valve means.

* * * * *

UNITED STATES PATENT AND TRADEMARK OFFICE
CERTIFICATE OF CORRECTION

PATENT NO. : 5,807,321
DATED : Sep. 15, 1998
INVENTOR(S) : Stoker et al.

Figure 1:
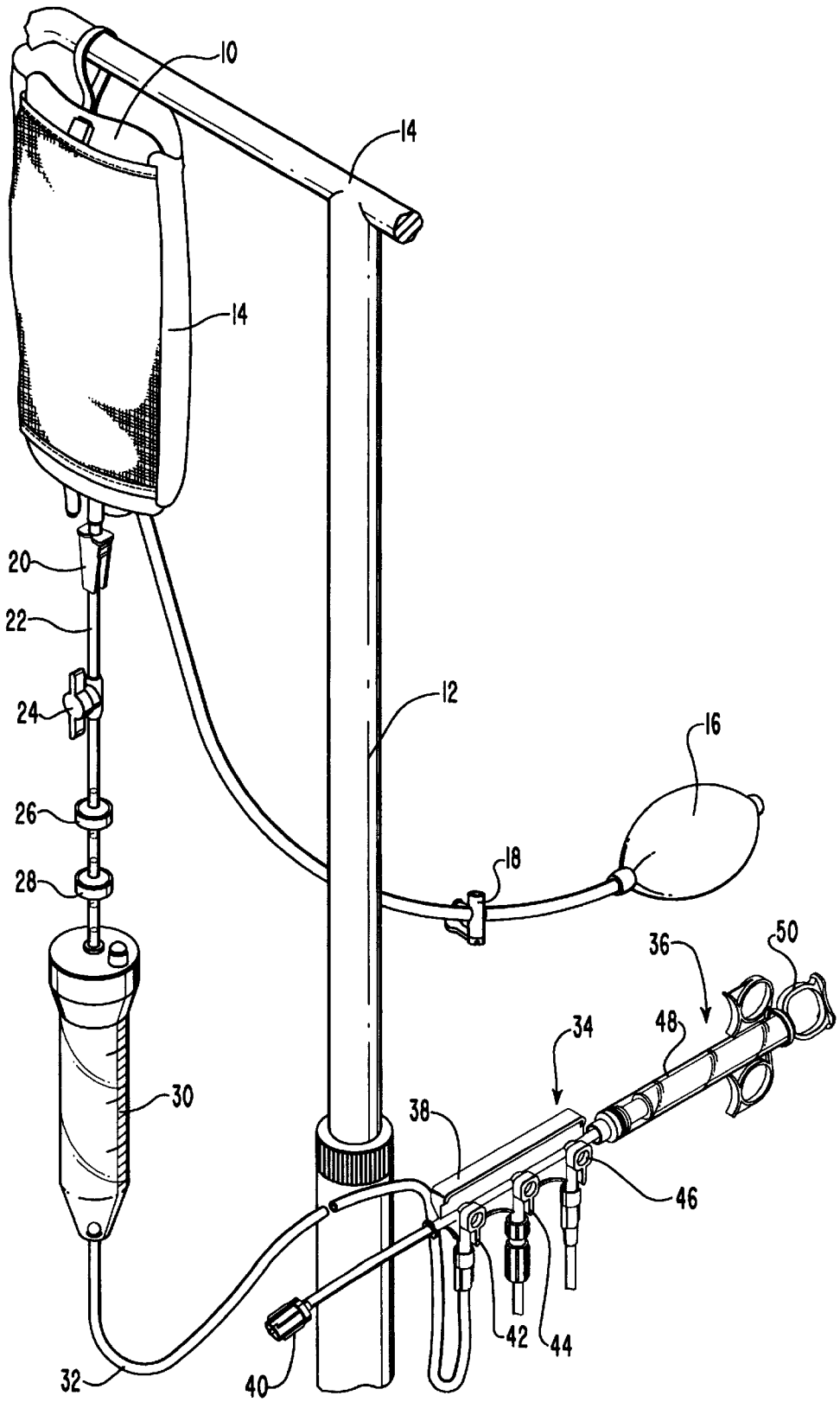
FIG. 1 is a perspective view of a typical prior art system.

It is certified that error appears in the above-identified patent and that said Letters Patent is hereby corrected as shown below:

Fig. 1, Item 12, at the top of the IV Pole (12) delete the label "14"

Fig. 7, change reference label "274" to --224--

Col. 2, line 9, after "flow" delete "into"

Col. 2, line 38, after "variety" insert --of--

Col. 5, line 58, before "noted" change "A" to --As--

Col. 25, line 35, before "data" change "nonvolitile" to --nonvolatile--

Col. 25, line 53, after "will" change "remains" to --remain--

Col. 35, line 6, after "controllable" change "moter" to --motor--

Signed and Sealed this

Seventh Day of March, 2000

Attest:

Attesting Officer

Q. TODD DICKINSON

Commissioner of Patents and Trademarks